US010420658B2

(12) United States Patent
Delaloye et al.

(10) Patent No.: US 10,420,658 B2
(45) Date of Patent: Sep. 24, 2019

(54) PROSTHESIS SEALS AND METHODS FOR SEALING AN EXPANDABLE PROSTHESIS

(71) Applicant: SYMETIS SA, Ecublens (CH)

(72) Inventors: Stéphane Delaloye, Bülach (CH); Jacques Essinger, St-Prex (CH); Jean-Luc Hefti, Cheseaux-Noréaz (CH); Youssef Biadillah, Genève (CH); Luc Mantanus, Lausanne (CH); Fabien Lombardi, Prilly (CH); Lionel Flaction, Chavan-nes-près-Renens (CH); Yutit Wanakoht, Meyrin (CH)

(73) Assignee: SYMETIS SA, Ecublens (CH)

( * ) Notice: Subject to any disclaimer, the term of this patent is extended or adjusted under 35 U.S.C. 154(b) by 186 days.

(21) Appl. No.: 14/775,666

(22) PCT Filed: Mar. 13, 2014

(86) PCT No.: PCT/EP2014/055044
§ 371 (c)(1),
(2) Date: Sep. 11, 2015

(87) PCT Pub. No.: WO2014/140230
PCT Pub. Date: Sep. 18, 2014

(65) Prior Publication Data
US 2016/0022444 A1    Jan. 28, 2016

Related U.S. Application Data

(60) Provisional application No. 61/779,744, filed on Mar. 13, 2013.

(51) Int. Cl.
A61F 2/24 (2006.01)
A61F 2/82 (2013.01)
A61F 2/95 (2013.01)

(52) U.S. Cl.
CPC .............. *A61F 2/82* (2013.01); *A61F 2/2418* (2013.01); *A61F 2/95* (2013.01);
(Continued)

(58) Field of Classification Search
CPC ............................................... A61F 2210/0061
See application file for complete search history.

(56) References Cited

U.S. PATENT DOCUMENTS 5,769,882 A    6/1998  Fogarty et al.
6,569,198 B1 *  5/2003  Wilson ................. A61F 2/2451
                                                        623/2.36
(Continued)

FOREIGN PATENT DOCUMENTS

EP          1262201 A1    12/2002
WO     WO 2008/070442 A1   6/2008
(Continued)

OTHER PUBLICATIONS

International Search Report, dated Sep. 4, 2014 for International Application No. PCT/EP2014/055044.

*Primary Examiner* — Jacqueline Woznicki
(74) *Attorney, Agent, or Firm* — Seager, Tufte & Wickhem LLP

(57) ABSTRACT

Embodiments of the present disclosure are related to devices and techniques for para-valve sealing of an expandable stent-valve implanted using a catheter. In some embodiments, a stent-valve is provided which comprises a seal sleeve/cuff containing material that swells when contacted by blood. A piercing tool may be included and used to permit a user to puncture the sleeve/cuff prior to introduction into a patient's body. In some embodiments, the sleeve/cuff has an integral tubular structure configured to withstand balloon expansion of the stent-valve during or after implantation. In
(Continued)

some embodiments, the seal is provided as a separate component from the stent-valve.

10 Claims, 19 Drawing Sheets

(52) U.S. Cl.
CPC . *A61F 2210/0061* (2013.01); *A61F 2220/005* (2013.01); *A61F 2220/0058* (2013.01); *A61F 2220/0075* (2013.01); *A61F 2230/0065* (2013.01); *A61F 2250/0056* (2013.01); *A61F 2250/0063* (2013.01); *A61F 2250/0069* (2013.01)

(56) References Cited

U.S. PATENT DOCUMENTS

| | | | | |
|---|---|---|---|---|
| 2002/0151953 | A1* | 10/2002 | Chobotov | A61F 2/954 623/1.11 |
| 2005/0137688 | A1* | 6/2005 | Salahieh | A61F 2/2418 623/2.11 |
| 2005/0283231 | A1* | 12/2005 | Haug | A61F 2/2418 623/2.11 |
| 2006/0004442 | A1 | 1/2006 | Spenser et al. | |
| 2007/0060998 | A1 | 3/2007 | Butterwick et al. | |
| 2010/0262231 | A1* | 10/2010 | Tuval | A61F 2/2412 623/2.4 |
| 2011/0093058 | A1* | 4/2011 | Vardi | A61F 2/07 623/1.15 |
| 2012/0303116 | A1* | 11/2012 | Gorman, III | A61F 2/2418 623/2.11 |
| 2013/0190857 | A1* | 7/2013 | Mitra | A61F 2/2418 623/1.23 |
| 2013/0197622 | A1* | 8/2013 | Mitra | A61L 31/145 623/1.15 |
| 2013/0274873 | A1* | 10/2013 | Delaloye | A61F 2/2409 623/2.18 |
| 2013/0331929 | A1* | 12/2013 | Mitra | A61L 31/145 623/2.11 |
| 2014/0243969 | A1* | 8/2014 | Venkatasubramanian | A61F 2/2412 623/2.38 |

FOREIGN PATENT DOCUMENTS

| | | |
|---|---|---|
| WO | WO 2010/083558 A1 | 7/2010 |
| WO | WO 2012/002228 A1 | 1/2012 |
| WO | WO 2013/033791 A1 | 3/2013 |
| WO | WO 2014/072439 A1 | 5/2014 |

* cited by examiner

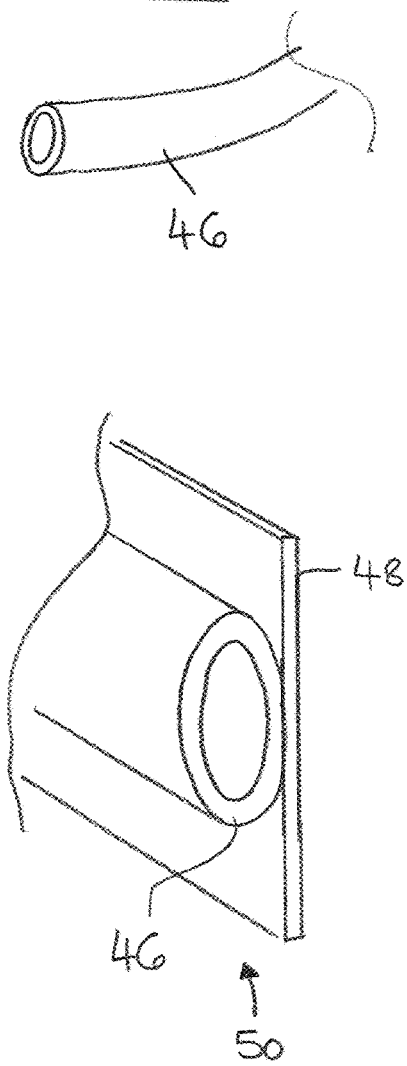
FIG. 3A
FIG. 3C
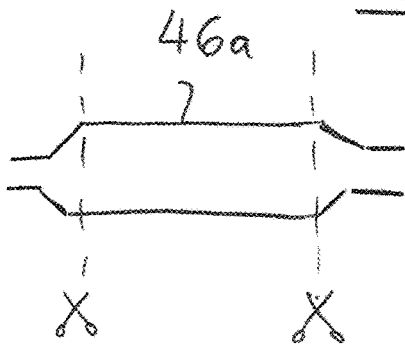
FIG. 3B
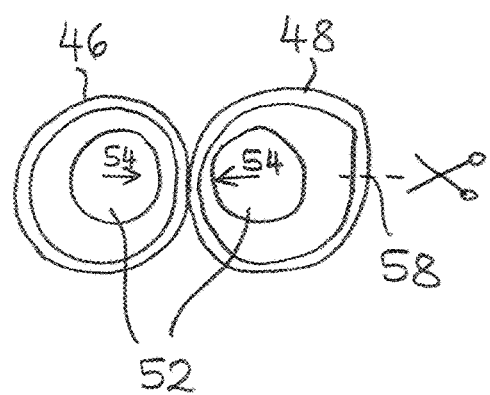
FIG. 3D

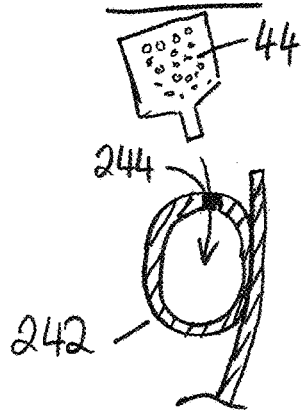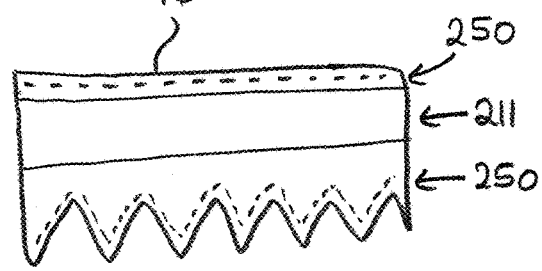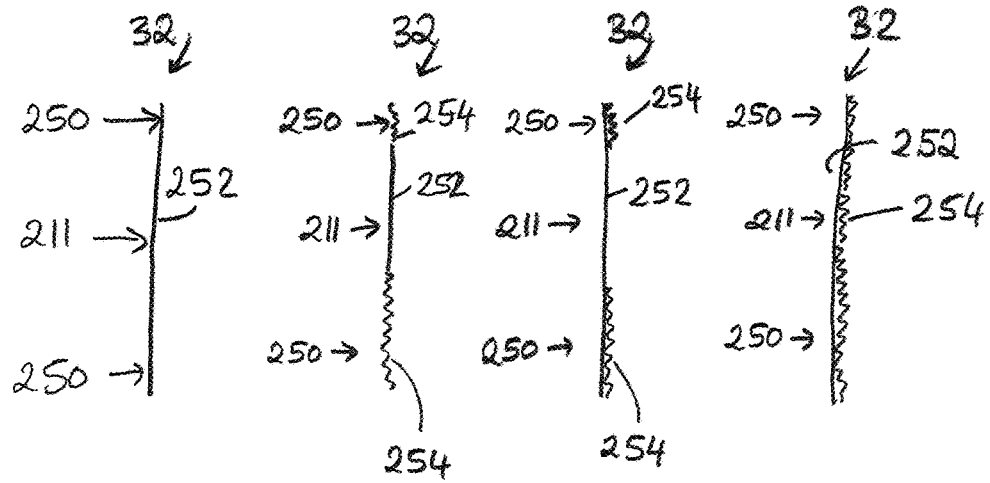
FIG. 23  FIG. 24
FIG. 25  FIG. 26  FIG. 27  FIG. 28

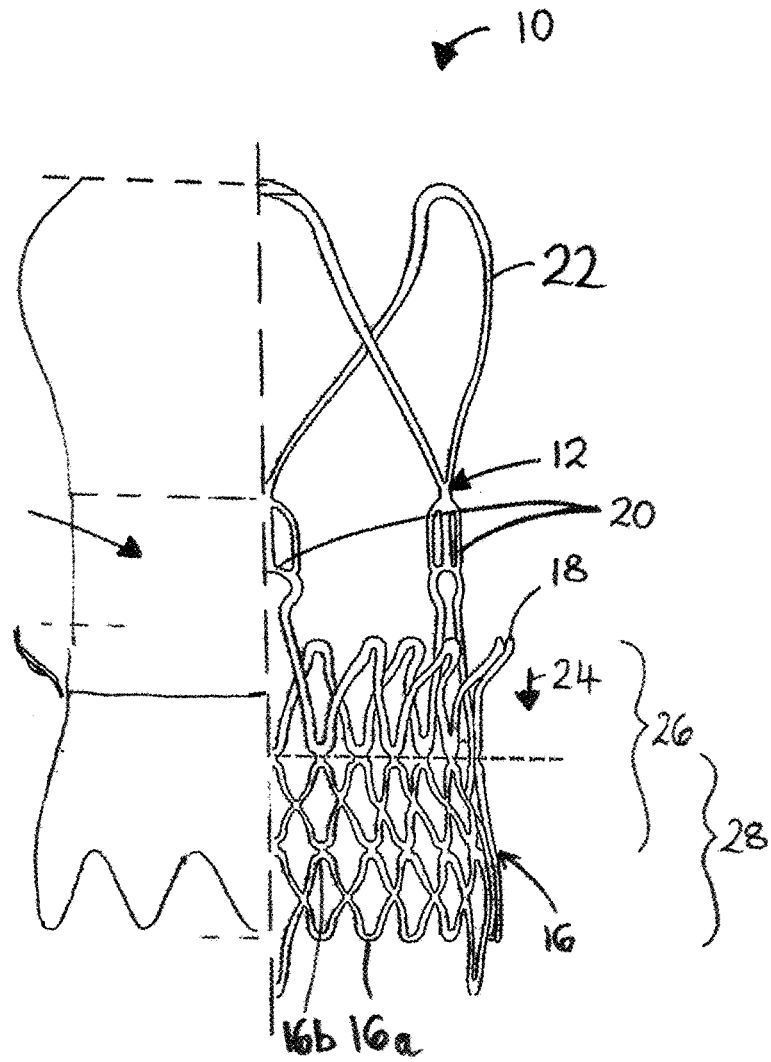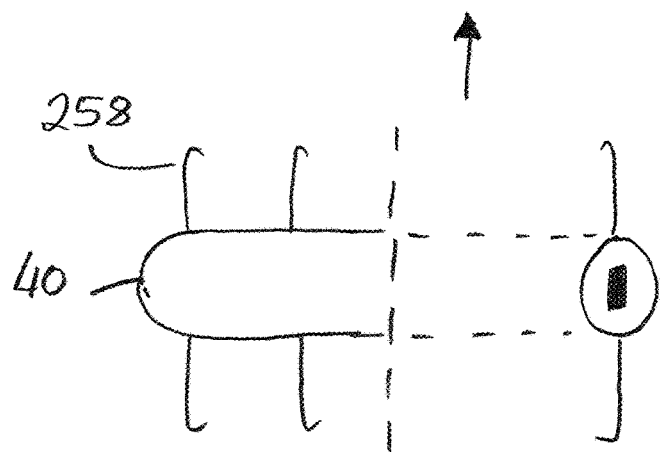
FIG. 29

PROSTHESIS SEALS AND METHODS FOR SEALING AN EXPANDABLE PROSTHESIS

CROSS REFERENCE TO RELATED APPLICATIONS

This application claims priority to International Patent Application No. PCT/EP2014/055044, filed Mar. 13, 2014, and entitled "Prosthesis Seals and Methods for Sealing an Expandable Prosthesis," which claims priority to U.S. Provisional Patent Application No. 61/779,744, filed Mar. 13, 2013, and entitled "Prosthesis Seals and Methods for Sealing and Expandable Prosthesis." The present application incorporates herein by reference the disclosures of each of the above-referenced applications in their entireties.

FIELD OF THE DISCLOSURE

The present disclosure relates to the field of stents implantable in the body. Embodiments have been devised to address problems encountered in the field of stent-valves, for example cardiac stent-valves (e.g., prosthetic heart valves). However, the concepts disclosed herein may have broader application to any stent or stented prosthesis where a seal is desired at an exterior surface of a stent.

BACKGROUND OF THE DISCLOSURE

Transcatheter valve implantation (for example, transcatheter aortic valve implantation (TAVI)) is an evolving technology for replacement valve therapy that (i) avoids the trauma of conventional open-chest surgery, and (ii) avoids the need for heart and lung bypass. In such a technique, a stent-valve is compressed and loaded into a delivery catheter. The delivery catheter is introduced to the desired site of implantation (for example at the heart) via a percutaneous route or via minimally invasive surgery. The stent-valve is expanded into the implantation position from or by the delivery catheter, and the delivery catheter is then withdrawn.

Despite the successes of transcatheter stent-valves, technological challenges remain. One such challenge is preventing retrograde leakage of blood around the stent-valve (so called para-valve leakage). The above-noted stents form a friction fit with the native anatomy to anchor the stent-valve in position, and are round in cross-section. However the native anatomy in which the stent is implanted is often off-round and is different for each person. Moreover, heavy calcification of the native anatomy may obstruct full deployment of any stent and make the native anatomy even more irregular. Thus, it can sometimes be difficult to provide a perfectly sealing fit between the stent-valve and the surrounding anatomy. Para-valve leakage is believed to be one of the factors affecting the long-term efficacy of the prosthetic valve, and possibly the life expectancy of the patient. One explanation is that the heart may have to work harder to compensate for some blood leaking retrograde at the entrance or exit of the heart. Therefore, addressing para-valve leakage is a significant challenge.

It is known to incorporate an external skirt or cover as part of the stent-valve. For example, the skirt is made of compressible biocompatible material, such as pericardial tissue or PET. The thicker the material of the skirt, the more able the skirt is to occlude gaps and effect a seal. However, a disadvantage is that such skirts add to the bulk of the stent-valve. A thick skirt makes the stent-valve problematic to compress to a desirably small size for implantation.

US-A-2005/0137688 is understood to describe compliant sacs disposed around the exterior of a stent, that are said to provide a more efficient seal along an irregular interface. The sacs may be filled with an appropriate material, for example, water, blood, foam or a hydrogel. Different arrangements of sacs are proposed in principle, but this document neither describes any specific construction technique nor does it describe handling of the fill material.

U.S. Pat. No. 5,769,882 is understood to describe an implantable expansible tubular vascular prosthesis carrying a form-in-place sealing layer for occluding at least a circumferential band at the interface between the prosthesis and the native tissue wall. In one example, the sealing layer comprises a hydrogel, arranged in a sleeve/cuff comprising a permeable membrane.

EP 1262201 is understood to describe an implantable vascular device having an external seal structure comprising a swellable hydrodel. In use, the hydrogel absorbs a mass of liquid so as to assume, as a result of the absorption, a certain degree of mechanical consistency. An example hydrogel has a polyvinyl alcohol (PVA) base, in combination with a polysaccharide.

WO-A-2008/070442 is understood to describe prosthetic heart valves, both expanding and non-expanding types, each having an anchoring sleeve that changes shape when the valve is implanted, to prevent migration of the valve. The anchoring sleeve is at least partly made of a material that swells due to absorption of body fluids. In examples, the sleeve is made of an inner material that swells upon contact with body fluids, and enclosed by a cover.

US-A-2007/0060998 and WO-A-2010/083558 are understood to describe delivery of a dispensable or releasable reactive sealing agent for endoluminal use around (at least substantially around) a prosthetic device within a body lumen. The reactive sealing agent is released or dispensed into a space between the prosthetic device and the lumen wall, in response to exertion of a dispensing pressure or by a configuration change causing the release. While different arrangements of dispensing capsules are proposed, reliable containment of the agent when the prosthesis is implanted at the heart likely are not ensured, especially in view of the constant movement and cyclic compression experienced by heart valves.

Accordingly, it would be desirable to address one or more of the above issues and/or provide a technique for mitigating para-valve (or para-stent) leakage without substantially affecting other desirable characteristics.

SUMMARY OF SOME OF THE EMBODIMENTS

The following disclosure presents a summary in order to provide a basic, non-limiting, understanding of some embodiments of the invention.

For example, in some embodiments of the present disclosure, a seal is provided for a prosthesis. The seal may be configured for obstructing para-prosthesis leakage. The prosthesis may, for example be a stent-valve (for example a cardiac stent-valve, such as an aortic stent-valve). The seal may comprise one or any combination of two or more of the following features, which are all optional. The list of optional features is bulleted by dashes ("—").

In some embodiments, the seal or a seal component is provided as a separate item from the prosthesis. The separate seal (e.g. component) may be mountable on the prosthesis prior to implantation of the prosthesis. For example, the seal (e.g. component) may be mountable on the prosthesis as part of a pre-implantation preparation process. The prosthesis and separate or non-integral seal or seal component may be provided and/or packaged together, for example, as a kit.

Alternatively, the seal may be provided as an integral part of the prosthesis.

Alternatively, a flowable seal material may be introduced into a seal sleeve or sleeve/cuff as part of a pre-implantation preparation process.

A pre-implantation preparation process may, for example, be carried out at the same hospital or clinic as the implantation procedure and/or within 2 hours or less before the implantation procedure (optionally about 90 minutes or less, optionally about 80 minutes or less, optionally about 70 minutes or less, optionally about 60 minutes or less, optionally about 50 minutes or less, optionally about 40 minutes or less, optionally about 30 minutes or less, optionally about 20 minutes or less, optionally about 10 minutes or less).

A pre-implantation preparation process may comprise a step of rinsing the prosthesis substantially clean of a storage solution in which the prosthesis is stored and/or provided. The step of mounting the seal on the prosthesis (if this step is implemented) may be carried out after the prosthesis rinsing step.

Continuing from the above list, the seal may comprise one or any combination of two or more of the following features, as well as the above-noted features, which are all optional:

The seal may comprise a swellable material that swells in response to contact with blood (or at least a blood component).

The seal may comprise a hollow sleeve and/or hollow cuff for containing the swellable material. The term "cuff" may refer to the intended arrangement of the seal around the prosthesis (for example, after mounting in the case of the mountable separate seal, or as provided when integral with the prosthesis). Throughout this specification the terms "sleeve/cuff" and "cuff/sleeve" are used to mean "sleeve and/or cuff" whether or not the "and/or" language is recited explicitly.

The sleeve/cuff may confine the swellable material captive within the sleeve/cuff. In some embodiments, the swellable material may be introduced into the sleeve/cuff during manufacture, and provided as a sleeve/cuff containing the swellable material. In other embodiments, the swellable material may be introducible into the sleeve/cuff as part of a pre-implantation preparation process (for example, as explained above, whether or not the seal is a mountable separate seal). In some embodiments, the swellable material is introducible by injecting into the interior of the sleeve/cuff (for example, injecting through the wall of the sleeve/cuff or through a dedicated port of the sleeve/cuff).

The sleeve/cuff may extend generally in a circumferential direction. In the case of a mountable separate seal, the sleeve/cuff may extend generally in a circumferential direction at least once mounted on the prosthesis.

The sleeve/cuff may define a single hollow interior space for swellable material, or the sleeve/cuff may be partitioned to define plural pockets or compartments for the swellable material. At least some of the pockets may communicate with each other, and/or at least some of the pockets may be closed spaces not in communication with any other pocket. In some embodiments, the internal partitioning may substantially prevent redistribution of the swellable material between pockets, or alternatively permit substantially free redistribution of the swellable material between pockets, or alternatively permit restricted redistribution of the swellable material between pockets. In some embodiments, the internal partitioning may be frangible so as to permit communication between two closed pockets upon rupture of the internal partitioning.

The sleeve/cuff may comprise a single wall, or the sleeve/cuff may comprise plural walls nested one behind, or within, another. At least one wall may comprise a single layer of material, and/or at least one wall may comprise plural layers of material (e.g. a multi-layered wall and/or a laminate).

The sleeve and/or cuff, or at least a wall or layer thereof, may comprise a region that is permeable or at least semi-permeable to liquid. The permeable/semi-permeable region may be configured to (i) allow communication therethrough of blood components or at least a blood component (for example, into the interior of the sleeve/cuff to cause the swellable material to swell), and/or (ii) obstruct passage therethrough of blood emboli (for example, to substantially prevent escape into the blood stream of any emboli that may form within the sleeve/cuff), and/or (iii) obstruct passage therethrough of swellable material particles (for example, to substantially prevent escape into the blood stream of any loose particles of the swellable material).

The permeable/semi-permeable region may have pores or other spaces referred to herein also as pores (e.g. perforations). The pore size (e.g. average pore size) may, for example, be not substantially greater than about 0.2 mm. Optionally, the pore size may be not substantially greater than about 0.15 mm, optionally not substantially greater than about 0.12 mm, optionally not substantially greater than about 0.11 mm, optionally not substantially greater than about 0.1 mm, optionally not substantially greater than about 0.05 mm, optionally between about 0.05 mm and about 0.02 mm, optionally about 0.1 mm, optionally not substantially greater than about 0.01 mm, optionally not substantially greater than about 0.009 mm, optionally not substantially greater than about 0.008 mm, optionally not substantially greater than about 0.007 mm, optionally not substantially greater than about 0.006 mm, optionally not substantially greater than about 0.005 mm, optionally not substantially greater than about 0.004 mm, optionally not substantially greater than about 0.003 mm, optionally not substantially greater than about 0.002 mm, optionally not substantially greater than about 0.001 mm.

In some embodiments, the permeable/semi-permeable region may be a layer of the sleeve/cuff.

In some embodiments, the permeable/semi-permeable region may extend over only a portion of the sleeve/cuff, and/or over only a portion of a wall of the sleeve/cuff, and/or a layer of the sleeve/cuff.

The permeable/semi-permeable region may comprise perforated film, for example, laser perforated film.

The (e.g. laser) perforated film may be a monolayer film, or a laminate of two or more layers.

The pore size of the (e.g. laser) perforated film may optionally have a variation of less than 20% from an average pore size, optionally less than 15% from an average pore size, optionally less than 10% from an average pore size, optionally less than 5% from an average pore size.

In some embodiments, the (e.g. laser) perforated film may have a thickness of not substantially greater than 0.05 mm. Use of such a thin film can contribute to achieving a compact sleeve/cuff for enabling the stent-valve to achieve a desirably small size for delivery by catheterization. Optionally the film thickness is not substantially greater than about 0.045 mm, optionally not substantially greater than about 0.04 mm, optionally not substantially greater than about 0.035 mm, optionally not substantially greater than about 0.03 mm, optionally not substantially greater than about 0.025 mm, optionally not substantially greater than about 0.02 mm, optionally not substantially greater than about 0.015 mm, optionally not substantially greater than about 0.01 mm, optionally not substantially greater than about 0.005 mm. In some embodiments, the film thickness may be between about 0.005 mm and about 0.015 mm, optionally between about 0.005 mm and about 0.01 mm, and optionally between about 0.006 mm and about 0.008 mm, optionally about 0.007 mm.

In some embodiments, the (e.g. laser) perforated film may have a strength (e.g. linear tensile strength) at least 50% of the film strength prior to laser perforation, optionally at least 60% of the strength prior to laser perforation, optionally at least 70% of the strength prior to laser perforation, optionally at least 80% of the strength prior to laser perforation, optionally at least 90% of the strength prior to laser perforation. Such characteristics can contribute to a strong film even with thin film thickness.

In some embodiments, the pores (or at least a majority thereof) in the (e.g. laser) perforated film are substantially round and/or have a cauterized perimeter and/or have a raised margin around their perimeter. Such a feature or features may contribute individually or in combination to film strength even with thin film thickness. A round pore shape can avoid sharp corners in the peripheral shape that could be points of stress concentration or lead to outward crack propagation. Cauterization of the material around the perimeter of the pore may also advantageously reduce risk of outward crack propagation. A raised margin of material around the pore perimeter may also provide additional material, and hence strength, surrounding the open area of the pore.

Continuing from the above list, the seal may comprise one or any combination of two or more of the following features, as well as any of the above-noted features, which are all optional:

The sleeve/cuff may comprise flexible material. The sleeve/cuff may comprise material that is elastically stretchable, and/or material that is substantially non-elastically-stretchable.

The swellable material may occupy only a portion of the (e.g. circumferential) length of the sleeve/cuff, for example, optionally not more than about 75%, optionally not more than about 60%, optionally not more than about 50%, optionally not more than about 40%, optionally not more than about 30%, optionally not more than about 25%, optionally not more than about 20%.

The sleeve/cuff may be transparent or translucent. The swellable material may have a distinctive color (at least when dry) enabling the position of the swellable material to be identified within the sleeve/cuff. Such identification may aid a practitioner in deciding where optionally to puncture the sleeve/cuff, if this technique is used, as described later.

The sleeve/cuff may have or comprise an integral tubular structure. As used herein, the term "integral tubular structure" may mean that the sleeve/cuff or a wall thereof or a layer thereof, or in the case of a laminate, at least a structural substrate within the laminate, is produced as an original integral tube around an axis passing along a centerline of the tube. As used herein, references to the sleeve/cuff having or comprising an integral tubular structure apply to at least a wall, or a layer, or at least a structural substrate of a laminate, whether or not mentioned explicitly, and whether or not the entire sleeve/cuff may have such a structure. For example, integral tubular structures may be made by extrusion of material in tubular form, or by blow molding a preform to define a tubular form.

In some embodiments, an integral tubular structure contrasts from a tube that is non-integrally formed around an axis passing along a centerline of the tube. Non-integral forming may include, for example, wrapping a film or sheet around an axis and securing portions to the film or sheet to define a hollow envelope enclosed by the wrapping, or by attaching two sheets to define an envelope. (Some embodiments including non-integral forming are also possible, and are illustrated herein.)

In some embodiments, using an integral tubular structure for the sleeve/cuff may enable the sleeve/cuff to achieve the otherwise conflicting requirements of desirably thin wall thickness, and good strength against bursting. Risk of bursting is often highest at join-lines of non-integral structures. Forming an integral tubular structure reduces the need for extensive join lines, in particular, a join line extending circumferentially around the prosthesis (in some embodiments, substantially around).

In some embodiments, in which the stent-valve is configured to be expanded to an operative configuration by expansion by an inflatable expansion balloon, providing a stent-valve with a seal sleeve/cuff comprising an integral tubular structure may be highly advantageous in enabling the seal sleeve/cuff to made desirably thin, yet have good strength and resistance to bursting should the seal be subject to the forces applied during the balloon-expansion, especially against the irregular or sharp contours of a calcified native anatomy Although not immediately intuitive, some embodiments of the present disclosure provide a technique of post-implantation balloon-expansion of an implanted prosthesis stent-valve carrying a swellable seal. Providing a stent-valve with a seal sleeve/cuff comprising an integral tubular structure may be highly advantageous in enabling the seal sleeve/cuff to made desirably thin, yet include strength and resistance to bursting should the seal be subject to the high forces applied during post-implantation balloon-expansion, especially against the irregular or sharp contours of a calcified native anatomy. For example, such forces may be greater than normally experienced by the seal during initial implantation (whether by self-expansion of the stent-valve, or by manual manipulation, for example, initial balloon expansion). Additionally or alternatively, it may permit a second implantation procedure (for example, even many years into the future), which may itself involve a valvuloplasty procedure using an expansion balloon to prepare for implantation of a further prosthesis. The fact that the current stent-valve comprises a seal configured to withstand balloon expansion (e.g. valvuloplasty) forces without risk of bursting, may continue to provide the patient with the full range of options for future treatment (which might not be available to a patient who has been implanted with a different type of swelling seal not designed to withstand a future balloon expansion and/or valvuloplasty procedure).

Continuing from the list above, the seal may comprise one or any combination of two or more of the following features, as well as any of the above-noted features, which are all optional.

Whether or not the sleeve/cuff is formed as or comprising an integral tubular structure, the sleeve/cuff may comprise a tubular extrusion or blow molded tubing. In other embodiments, the sleeve cuff may comprise an envelope structure, for example, formed by a film or sheet folded and attached to itself to substantially enclose a volume, or at least two sheets attached to define an envelope. Such an envelope structure may differ from an integral tubular structure.

In addition to, or as an alternative to, the above, the sleeve/cuff may be configured to be able to withstand post-implantation balloon expansion of the stent-valve against a calcified anatomy without substantial loss of structural integrity of the hollow sleeve/cuff. This can provide similar advantages for permitting balloon expansion (e.g. post-implantation balloon expansion) and/or suitability for a future valvuloplasty procedure.

The hollow sleeve/cuff may be formed from or using a tubular segment from an inflatable cardiac valvulopasty balloon. Such balloon material already has desirable characteristics of being thin-walled yet strong to resist bursting when the balloon is inflated and bears directly against hard, irregular and sharp calcifications of a calcified vascular anatomy. The balloon material is also established as being bio-compatible and suitable for introduction into, and for direct contact with, the human vasculature. Optionally, the material may be laser-perforated, depending on whether it is desired to provide a permeable (or at least semi-permeable) characteristic.

The sleeve/cuff may be formed by a method including providing an elongate hollow tubular member (optionally with an integral tubular structure), introducing the swellable material into the interior of the tubular member, and optionally bending the elongate tubular member to form a substantially toroid shape (e.g. when mounted on the prosthesis).

The opposite ends of the (e.g. bent) elongate tubular member may be secured together (for example, by fusion, welding, or adhesive) to define a closed-loop toroid form, whether or not the ends of the tube communicate openly with each other as a continuous open interior space. Alternatively, the opposite ends of the (e.g. bent) elongate tubular member may remain disconnected from each other, even after mounting on the prosthesis.

The hollow sleeve/cuff, or at least a layer or wall thereof, may be liquid-tight, at least prior to use of the prosthesis.

The hollow sleeve/cuff, or at least a layer or wall thereof, may comprise polymeric material and further comprise a diffusion barrier layer to obstruct diffusion of liquid through the sleeve/cuff wall and into the space containing the swellable material.

The hollow sleeve/cuff, or at least a layer or wall thereof, may comprise a laminate of (1) plastics film and (2) a diffusion barrier layer to obstruct diffusion of liquids from outside the hollow sleeve/cuff to the hollow interior. The diffusion barrier optionally is formed either on an interior face of the sleeve/cuff or a layer or wall thereof (e.g. the hollow interior face), or as a non-surface layer of the laminate. Such positioning of the diffusion barrier layer may protect the integrity of the diffusion barrier layer during production and assembly of the prosthesis, enabling easier handling.

The diffusion barrier material of either of the above may be of or comprise a metal or metal compound (e.g., an oxide).

The metal or metal compound may be formed by plasma vapour deposition. The thickness of the layer may be optionally less than 100 nm, optionally less than 50 nm, optionally less than 10 nm.

The diffusion barrier layer may be configured to remain in position on the prosthesis when the prosthesis is implanted.

Additionally or alternatively, at least a portion of the sleeve/cuff (or at least a portion of a layer or wall thereof) may be configured to be removable to define an area through which liquid (e.g. blood) may be admitted, in use, for causing the swellable material to swell. The removable portion may, for example, be a portion of the or a liquid-tight layer or wall.

Additionally or alternatively, the sleeve/cuff material is configured to be pierced in use, prior to introduction into the body of a patient, to create liquid-admitting punctures in the sleeve/cuff material.

The prosthesis may be provided as part of a kit including a piercing tool usable to pierce the sleeve/cuff to form liquid-admitting punctures in the cuff. The piercing tool may comprise at least one pin or other sharp projection. The (or each) pin or protection may be dimensioned to permit puncturing of the sleeve/cuff without damaging other operative portions of the prosthesis (for example, without damaging leaflets of a stent-valve). The piercing tool may, for example, comprise a roller carrying the at least one (and preferably plural) pin or other sharp projection. The roller may be configured to be rollable over a region of the cuff/sleeve to effect the piercing action.

In some embodiments, the sleeve/cuff may be pierced before, during, or after, loading of the prosthesis (e.g. stent-valve) into a delivery catheter. In some examples, the delivery catheter includes a sheath within which the prosthesis (e.g. stent-valve) is at least partly contained when loaded (or during loading). The sheath may include at least one (and optionally a plurality) of apertures aligned with the sleeve/cuff, and through which the piercing tool may be introduced to pierce the sleeve/cuff while in situ in the delivery catheter.

In one example condition of a stent-valve prior to introduction of the stent-valve into the body of a patient, the stent-valve has a seal sleeve/cuff containing a swellable material. The sleeve/cuff is liquid impermeable except for at least one (and optionally a plurality) of liquid-admitting punctures made therein, for admitting liquid into the seal. Additionally or alternatively, the sleeve/cuff is made of liquid-impermeable material, the sleeve/cuff having one or more liquid admitting punctures made therein for admitting liquid into the seal.

In one example condition of a stent-valve prior to introduction of the stent-valve into the body of a patient, the stent-valve according to some embodiments includes a seal sleeve/cuff containing a swellable material. The swellable material is at least partly hydrated or wetted by liquid (e.g., prior to introduction of the stent-valve into the body). The sleeve/cuff may be constrained against substantial expansion by being constrained within a sheath of a delivery apparatus. The hydrating or wetting liquid may, for example, be saline. Allowing the seal sleeve/cuff to at least partly hydrate or become at least party wetted prior to introduction into the body may enable more efficient swelling of the material, and therefore of the sleeve/cuff, when the stent-valve is implanted. It can avoid the need for the seal to have to become wetted by liquid only on implantation. For example, speed of wetting and/or swelling may be a consideration if the liquid-admitting apertures (e.g.

punctures) in the sleeve/cuff are relatively small and/or if a relatively "slow" hydrating/swelling material is used within the sleeve/cuff.

Additionally or alternatively to the above, in one example condition of a stent-valve prior to introduction of the stent-valve into the body of a patient, the stent-valve is loaded at least partly into a delivery catheter. The delivery catheter comprises a containment sheath encompassing at least a portion of the stent-valve at which the seal is located, the containment sheath being at least partly filled with liquid, and the swellable material being exposed to the liquid, the containment sheath obstructing expansion of the seal. The liquid may, for example, be saline.

The seal may further comprise a skirt secured to the hollow sleeve/cuff, for example, using an attachment that does not puncture the cuff. Example attachments may include one or more of: fusion; welding, adhesive. The skirt may itself be attached to the stent, for example, by sutures. The skirt may provide a means by which the seal is fixed to the stent. Such a technique can enable the seal to be secured fixed to the stent, without risk that the stent fixings may compromise the integrity of the cuff.

The stent-valve (optionally all of the stent, valve-leaflets, and seal) may be compressible to a compressed configuration for delivery, and expandable to an operative configuration at implantation. In some embodiments, the stent is a self-expanding type that self-expands at least partly towards (and preferably self-expands entirely to) the operative configuration. Additionally or alternatively, the stent may be manually manipulable (e.g. plastically expandable) to the operative configuration, for example, using an expansion balloon or other expanding device or foreshortening device. The material of the stent, in either case, may for example be selected from one or more of: shape memory material; shape memory metal alloy; nitinol; steel, nickel-chromium (containing) alloy; chromium-cobalt (containing) alloy.

As mentioned previously above, the seal may be provided as a separate item from the prosthesis (e.g. stent-valve), and be mountable to the stent-valve, for example, as part of a pre-implantation preparation process. The seal and prosthesis may be provided and/or packaged together, for example, as a kit.

Various techniques are envisaged for mounting a separate seal to the prosthesis.

One mounting technique may be using adhesive, for example, an adhesive surface that is provided on the prosthesis and/or the seal. The adhesive surface may initially be protected by a release sheet or strip that is removable (e.g. peelable) from the adhesive surface, to expose the adhesive surface ready for attaching the seal to the prosthesis.

Additionally or alternatively, the prosthesis may comprise a dedicated seal accommodation region to which the seal is mountable.

The seal accommodation region may comprise an adhesive surface or a landing surface for adhesive engagement as aforementioned.

Alternatively, the seal accommodation region may comprise a substantially continuous, or a discontinuous, accommodation channel for receiving at least a portion of the seal. A discontinuous channel may be formed, for example, by a series of spaced apart loops similar to clothing belt loops. Each loop may be relatively short in circumferential extent and/or the number of loops may be relatively small, to define a relatively small mark/space ratio (e.g. closed-area/open-area ratio) of less than 1, optionally less than about 0.75, optionally less than about 0.5, optionally less than about 0.25. Alternatively, each loop may have a circumferential length such that, and/or the number of loops may be relatively high such that, the ratio is at least about 1, optionally at least about 1.25, optionally at least about 1.5, optionally at least about 1.75, optionally at least about 2, optionally at least about 2.5, optionally at least about 3. A substantially continuous channel may be formed, for example, by one of more of: a tubular structure; a circumferential flap; an open sided channel; a circumferential envelope or pocket.

A loading filament (e.g. of suture wire), may be pre-laid within the accommodation channel to facilitate loading of the seal into the channel. For example, one end of the loading filament may be attachable to the seal (for example, to one end of an elongate seal). Pulling on the opposite end of the loading filament may draw the seal into the channel.

The accommodation channel may include one or a plurality of openings and/or clearances for admitting blood to the seal. At least some of the openings and/or clearances may, for example, be arranged: (i) facing substantially or at least partly towards the prosthesis blood outlet end; and/or (ii) facing substantially or at least partly towards the prosthesis blood inlet end; and/or facing substantially in a generally radial inward and/or radial outward direction. The openings and/or clearances, however arranged, may optionally be permanently open such that the openings and/or clearances do not substantially prevent entry of liquid to the accommodation channel. The openings and/or clearances, however arranged, may have a size that does not substantially obstruct communication therethrough.

The accommodation region (e.g. accommodation channel) may optionally form part of or be coupled to an outer skirt fitting on an exterior surface of the prosthesis. The skirt may optionally comprise film, or fabric, or a combination of film and fabric.

The outer skirt may optionally be permanently attached to an inner skirt positioned within the prosthesis. The permanent attachment may be provided by, for example, welding, adhesive or suturing. The inner and outer skirts may be attached together along at least one line (or intermittent line) that is generally continuous at least in a circumferential direction around the prosthesis. Such a line of attachment can enhance the prevention of leak paths for blood that could otherwise exist between the inner and outer skirts were the skirts not so attached.

Optionally, and no matter how the seal is provided, in some embodiments the seal may comprise swellable material provided in the form of, or comprising, beads. The term "bead" is used herein to refer to any rounded or bulbous shape, including but not limited to spherical. Use of beads may facilitate migration of the material within the seal, for example, during swelling or under the influence of swelling, towards regions of free space or in which the seal is less confined, for example, corresponding to potential leak paths around the exterior of a stent-valve. Optionally, the beads may be microbeads.

Additionally or alternatively, whether or not the swellable material comprises beads, in some embodiments, prior to swelling (e.g. prior to hydration), at least a majority of particles of the swellable material (e.g. beads) may have a transverse dimension (e.g. diameter) of not substantially less than about 0.005 mm, optionally not substantially less than about 0.01 mm, optionally not substantially less than about 0.02 mm optionally not substantially less than about 0.03 mm, optionally not substantially less than about 0.05 mm, optionally not substantially less than about 0.06 mm, optionally not substantially less than about 0.07 mm, optionally not substantially less than about 0.08 mm, optionally not substantially less than about 0.09 mm. Optionally at least 75% of the particles have a size as defined, and optionally substantially all of the particles.

Additionally or alternatively, whether or not the swellable material comprises beads, in some embodiments, prior to swelling, at least a majority of particles of the swellable material (e.g. beads) may have a transverse dimension (e.g. diameter) greater than an aperture size (e.g. pore size) of a semi-permeable material forming at least a portion of a container for containing the beads/particles. Such an arrangement can be effective in obstructing escape of the beads/particles from the seal. The transverse dimension of the beads may optionally be at least 1.5 times the aperture size, optionally at least double the aperture size, optionally at least three times the aperture size. Optionally at least 75% of the particles have a size as defined, and optionally substantially all of the particles.

Additionally or alternatively, whether or not the swellable material comprises beads, in some embodiments, after swelling (e.g. after hydration), at least a majority of particles of the swellable material (e.g. beads) may have a transverse dimension (e.g. diameter) of not substantially greater than about 0.1 mm, optionally not substantially greater than about 0.09 mm, optionally not substantially greater than about 0.08 mm, optionally not substantially greater than about 0.07 mm. With such a size constraint, even should particles escape from the confines of the seal, and enter the blood stream, it is believed that the particles are small enough not to present any significant embolism risk for the patient. Many conventional embolism-protection filters are configured only to trap particles of about 0.1 mm, or greater, in size that are considered to be an embolism risk in the blood stream. Optionally at least 75% of the particles of swellable material have a size as defined, and optionally substantially all of the particles.

Additionally or alternatively, the swellable material may have a swelling capacity to enable an increase in volume of at least about 64 times its dehydrated volume. The volume swelling factor may be represented by an equilibrium swelling volume ratio "qv" of at least about 64. In some embodiments, qv may be in the range of about 64 to about 216. A qv value of 64 may correspond to a linear swelling change of 4. A qv value of 216 may correspond to a linear swelling change of 6.

Additionally or alternatively, the time duration for the swellable material to achieve full swelling when contacted by blood at body temperature (for example, when the material is free and/or when the material is contained within a semi-permeable sleeve/cuff as aforesaid), may be at least 5 minutes. Such a characteristic may provide sufficient time to compress and/or load a stent-valve, for example, while the seal is exposed to liquid (e.g. saline) without significant or too great swelling occurring. Additionally, or alternatively, the time duration may be not substantially greater than about 15 minutes. Such a characteristic may provide sufficiently rapid physical swelling of the material upon implantation, to enable the effect of the seal to be observed and judged during the normal duration of a procedure on the patient, and/or without prolonging the procedure unreasonably.

Additionally or alternatively, a skirt for a stent-valve comprises a first sheet of material attached or to be attached to a stent, and a second sheet of material. The second sheet of material may be configured such that, at least when attached to the first sheet of material, the attachment between the sheets stresses at least one of the sheets to encourage bulging of one sheet away from the other.

Further embodiments of the disclosure may relate to a method of production of a prosthesis (e.g. a stent-valve), optionally as defined by any one or any combination of two or more of the foregoing aspects and features. The method may comprise one or any combination of two or more of the following steps and/or features, which are all optional.

A seal of, or for, the prosthesis may be provided comprising a sleeve/cuff containing a swellable material. The sleeve/cuff may optionally be a sealed liquid tight sleeve/cuff, and/or the sleeve/cuff may be provided within a sealed liquid-tight container.

The seal may be attached to the prosthesis as an integral part of the prosthesis, or the seal may be provided as a separate component that is attachable to the prosthesis (for example, as part of a pre-implantation preparation process), or the seal may comprise at least one component that is introducible to (e.g. injectable into) a respective region of the prosthesis (for example, as part of a pre-implantation preparation process).

During the method of production, after assembling the components of the prosthesis (e.g. a stent, one or more prosthetic valve leaflets, and optionally the seal if provided in integrally attached form), the stent-valve may be immersed into a liquid. For example, the liquid may be a sterilizing liquid and/or a preservative liquid for packaging the stent-valve ready for use.

The liquid-tight sealed sleeve/cuff may prevent the liquid from contaminating the swellable material of the seal prior to intended use.

The liquid may be toxic to the human blood stream (for example, intended to be rinsed or otherwise cleaned off the prosthesis (e.g. stent-valve) before the prosthesis is introduced into a patient's body).

A tubular sleeve/cuff of the seal (and/or a wall and/or a layer and/or a structural substrate of a laminate thereof) may be formed by an integral tubular forming technique. Example techniques may include tubular extrusion and/or blow molding.

A tubular sleeve/cuff of the seal (and/or a wall and/or a layer and/or a structural substrate of a laminate thereof) may be obtained from a segment of a valvuloplasty balloon.

A tubular sleeve/cuff may be provided by the steps including providing an elongate hollow tubular member (optionally with an integral tubular structure), introducing the swellable material into the interior of the tubular member. Optionally the steps further include bending the elongate tubular member to form a substantially toroid shape.

The opposite ends of the (e.g. bent) elongate tubular member may be closed (for example, by fusion, welding or adhesive). Additionally or alternatively, the opposite ends of the (e.g. bent) elongate tubular member may be secured together (for example, by fusion, welding, or adhesive) to define a closed-loop toroid form. The opposite ends may be sealed closed to define a non-continuous interior of the sleeve/cuff at the join in the toroid, or they may communicate with each other to define a continuous open interior across the join.

A diffusion barrier layer may be formed on a tubular sleeve/cuff of the seal, or on a material blank used to form the tubular sleeve/cuff, and/or on other cover material for a seal comprising swellable material.

The diffusion barrier layer may be or comprise a metal or metal compound.

The diffusion barrier layer may be formed by plasma vapour deposition.

The method may include sterilizing the seal, and/or sterilizing a component used to form the liquid-tight sealed sleeve/cuff containing swellable material, by irradiation.

The method may include sterilizing the prosthesis (e.g. stent-valve), after assembly, by contacting the prosthesis with a sterilizing fluid, e.g. immersing the stent-valve in a sterilization liquid. If provided, the liquid-tight sealed sleeve/cuff may prevent liquid contamination of the swellable material. The sterilization liquid may optionally comprise an aldehyde, optionally glutaraldehyde.

The method may include storing the prosthesis (e.g. stent-valve), ready for use, in liquid preservative. If provided, the liquid-tight sealed sleeve/cuff may prevent liquid contamination of the swellable material. The liquid preservative may optionally comprise an aldehyde, optionally glutaraldehyde.

The method may include sterilizing a sealed sleeve/cuff, and sterilizing swellable material therein, using a different sterilizing technique from the remainder the prosthesis (e.g. stent valve). For example, the sleeve/cuff, and the swellable material may be sterilized using radiation. The remainder of the prosthesis (e.g. stent-valve) may be sterilized by contacting the prosthesis with a sterilizing liquid (or other sterilizing fluid).

In addition to or alternatively to any of the foregoing, a method of producing a prosthesis or a seal for or of a prosthesis, may comprise providing a wall or layer of material, the material including at least a laser-perforated region. The wall or layer of material may be provided as, or be formed into, a sleeve/cuff of a seal for containing a swellable material that swells when contacted by blood. The laser-perforated region may extend over substantially the entire area of the material, or at least a majority of the material, or over only a selected zone leaving a further zone without any perforations.

In addition to or alternatively to any of the foregoing, a method of producing a prosthesis or a seal for or of a prosthesis, may comprise the step of laser perforating a region of material. The material may be in the form of, or subsequently formed into, a sleeve/cuff of a seal for containing swellable material that swells when contacted by blood. The step of laser perforating may comprise perforating substantially the entire area of the material, or at least a majority of the material, or only a selected zone leaving a further zone without any perforations.

Further embodiments of the present disclosure may relate to a method of preparing and/or using a prosthesis (e.g. stent-valve) for implantation, the prosthesis optionally as defined and/or produced by any one or any combination of two or more of the foregoing aspects and features. The method of using and/or preparing may comprise one or any combination of two or more of the following steps and/or features, which are all optional:

providing (i) the prosthesis (e.g. stent-valve) stored in a storage solution, and (ii) a seal comprising a material that swells when contacted. Optionally the seal is included as part of the prosthesis. Alternatively, at least a component of the seal is provided as a separate item from the prosthesis, and is mountable to, and/or introducible to, and/or injectable into the prosthesis as part of the method. For example, the seal or seal component may be provided as a separate component mountable to the prosthesis, or alternatively as a flowable component that is injectable into a seal part of the prosthesis.

The seal may comprise a material that swells when contacted by liquid and a sleeve/cuff or cover. The sleeve/cuff and/or cover may protect the seal from contact by the storage solution, if the seal is provided as part of the prosthesis within the storage solution.

rinsing the stent-valve to clean the stent-valve of the storage solution;

after rinsing, piercing the sleeve/cuff or cover at one or more positions to break the integrity of the sleeve/cuff or cover, in order to allow blood to contact the swellable material upon implantation;

after rinsing, mounting the seal to the prosthesis (if the seal is provided as a separate component).

additionally or alternatively, after rinsing, compressing and/or loading the stent-valve into a delivery apparatus for introduction into the body;

additionally or alternatively, after rinsing and while the stent-valve is outside a human body, exposing the swellable material to, and/or contacting the swellable material with, liquid to allow at least partial wetting or hydration of the swellable material; and the step of exposing may be carried out before, or during, or after the step of compressing. For example, the liquid may be liquid within which the stent-valve is at least partly immersed (i) during compressing and/or loading, or (ii) within the delivery catheter.

In a closely related aspect, the invention relates to a further method of using a stent-valve for implantation, the stent-valve optionally as defined and/or produced by any one or any combination of two or more of the foregoing aspects and features. The method of using may comprise one or any combination of two or more of the following steps and/or features, which are all optional:

providing a stent-valve that is compressible to a compressed configuration for delivery, and expandable to an operative configuration for implantation, the stent-valve comprising a stent, a plurality of leaflets defining a prosthetic valve, and a seal for sealing against surrounding tissue, the seal comprising a swellable material that swells when contacted by blood (and the seal being optionally a part of the prosthesis, or at least a component of the seal being a separate component that is mounted to or injected into the prosthesis as part of the method);

introducing the stent-valve into the body in its compressed configuration using a delivery device, and advancing the stent-valve to a desired implantation site;

causing the stent-valve to expand at the implantation site, from the compressed configuration to its operative configuration;

observing one or more characteristics of the operative stent-valve; and in dependence on the result of the observation at step (d), performing post-implantation balloon expansion of the stent-valve.

Features and advantages of some of the embodiments of the disclosure, include:

facilitating a seal construction that is able to swell to automatically seal gaps between the stent-valve and the surrounding tissue, even in the case of an irregular anatomy;

facilitating safe post-dilation of the stent-valve as desired, without significant risk of seal rupture;

facilitating long storage times of a stent-valve without risk of contaminating the swellable material of the seal by toxic storage solution;

facilitating thorough sterilization of a stent-valve without contaminating or otherwise compromising the swellable material of a seal;

facilitating simple yet effective activation of the swellable material of a seal without having to separate components;

facilitating early partial hydration or wetting of a swellable seal before implantation, to reduce the burden of seal to access liquid only at the instant of deployment at the implantation site;

avoiding the need for any rupture of a capsule membrane during the implantation process, by facilitating exposure of a swellable seal material to liquid prior to introduction into the body, and carrying out such exposure while the seal is constrained against expansion.

Additional and/or independent embodiments and features of the disclosure are included in the claims.

Although certain features and aspects of the invention are highlighted in the foregoing summary and in the appended claims, protection is claimed for any novel concept described herein and/or illustrated in the drawings, whether or not emphasis is placed thereon.

BRIEF DESCRIPTION OF THE DRAWINGS

Non-limiting embodiments of the invention are now described with reference to the accompanying drawings, in which:

FIG. 3a is a schematic perspective view of an elongate tubular member for use in the production of a seal according to some embodiments of the disclosure.

FIG. 3b is a schematic section illustrating obtaining the tubular member from a valvulopasty balloon according to some embodiments of the disclosure.

FIG. 3c is a schematic partial perspective view of a sub-assembly including tubing and outer skirt material according to some embodiments of the disclosure.

FIG. 3d is a schematic section illustrating an example of forming the sub-assembly of FIG. 3c, according to some embodiments of the disclosure.

FIG. 23 is a schematic section illustrating swellable material in the form of flowable material, such as beads.

FIG. 24 is a schematic side view of a skirt with attachment zones.

FIGS. 25, 26, 27 and 28 are schematic sections showing alternative example constructions of skirt wall.

FIG. 29 is a schematic partial section similar to FIG. 1, but showing an alternative technique for mounting a separate seal.

DETAILED DESCRIPTION OF EMBODIMENTS OF THE INVENTION

Figure 1:
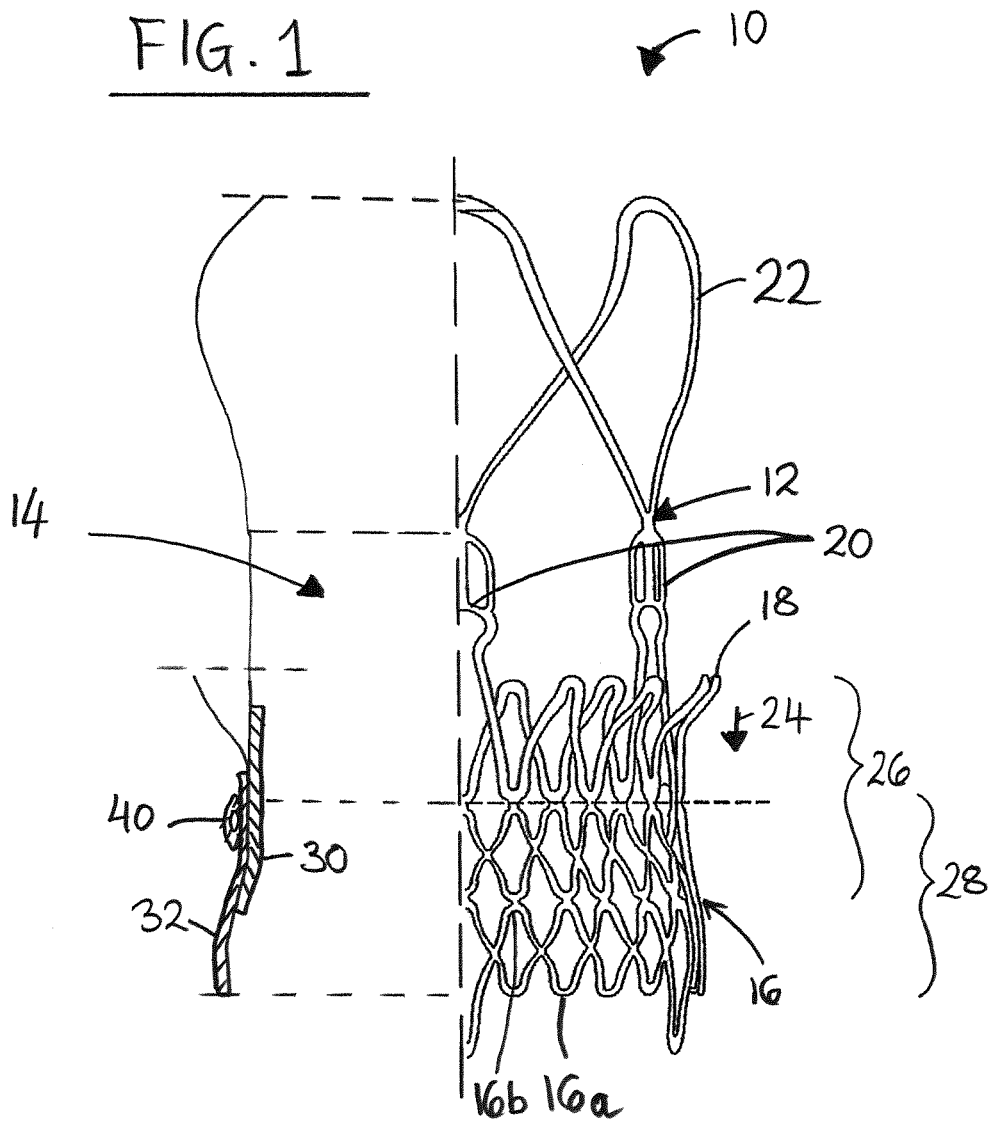
FIG. 1 is a schematic drawing illustrating a stent-valve 10 with which some embodiments of the present disclosure are suitable to be used. The figure is broken along a centre-line of the stent-valve. The stent-structure is shown to the right, and a profile showing the positions of the valve, skirt and seal is shown to the left.

Referring to FIG. 1, a stented prosthesis according to some embodiments is illustrated in the form of a stent-valve 10. A seal 40 (described further below) may be provided for sealing against surrounding tissue when the stent-valve 10 is implanted. The stent-valve 10 may be cardiac stent-valve, for example, an aortic stent-valve, a mitral stent-valve, a pulmonary stent-valve or a tricuspid stent-valve, for implantation at the respective valve position in a human heart.

The stent-valve 10 may optionally comprise biological tissue (for example, pericardium (such as porcine pericardium and/or bovine pericardium) and/or natural cardiac valve leaflets (for example, natural porcine cardiac valve leaflets, optionally attached to a portion of natural cardiac wall tissue). The biological tissue may be fixed, for example, using glutaraldehyde.

The stent-valve 10 may be compressible to a radially compressed condition (FIG. 8) for delivery using a delivery catheter, and be expandable to an operative or expanded condition (as shown) at implantation. The stent-valve 10 may comprise a stent 12 carrying a plurality of leaflets defining a valve 14 (the position of which is depicted schematically by the bounding phantom lines). Various geometries of stent 12 may be used. In some embodiments, the stent 10 may include one of more of: a lower tubular or crown portion 16, an upper crown portion 18, a plurality of upstanding commissural supports 20, and a plurality of stabilization arches 22. In use, the lower portion 16 of the stent 12 may be configured to be deployed after the other regions of the stent 12. For example, the arches 22, the supports 20 and the upper crown 18 may be deployed at least partly before the lower portion 16 (in that order, or in reverse order, or in a different order). At the very least, once the upper crown 18 has been at least partly deployed, the stent 12 may be urged and/or displaced in the direction of arrow 24 to seat the upper crown 18 against native leaflets at the implantation site. Deploying the lower portion 16 last fixes the stent 12 in its final position.

The lower portion 16, and optionally a portion of the upper crown 18, may be formed by a lattice structure of the stent. The lattice structure may define cells or apertures, for example, generally diamond-shaped apertures.

The native leaflets may generally overlap a portion 26 of the stent. The native valve annulus may overlap a portion 28 of the stent.

Optionally, the stent-valve 10 may further include an inner skirt 30 communicating with the leaflets 14 and carried on an interior of the stent 12. Additionally or alternatively, the stent-valve 10 may further comprise an outer skirt 32 carried on an exterior of the stent 12. When both skirts are provided, the skirts may partially overlap. The skirts may be offset such that one skirt (e.g. the outer skirt 32) extends further towards a lower extremity of the stent 12 than the other (e.g. inner skirt 30). Additionally or alternatively, one skirt (e.g. the inner skirt 30) extends further towards an upper extremity of the stent 12 than the other (e.g. outer skirt 32). The skirts may be of any suitable flexible and/or compliant material, for example, fabric (e.g. of PET) or of biological tissue (e.g. of pericardium).

Optionally, the inner skirt 30 and the outer skirt 32 may be attached directly to each other along at least one substantially continuous or discontinuous line of attachment. The attachment may, for example, be by one of more of: suturing, welding, fusion, adhesive. The line of attachment may optionally extend around the entire circumference of the stent-valve. The attachment may mitigate risk of leakage of blood in the spaces of the stent between the inner and outer skirts 30 and 32.

Optionally, at least the outer skirt 32 is positioned to leave the upper crown 18 substantially unobscured by the outer skirt 32. Such an arrangement may assist good blood flow to the coronary arteries (for example, in the case of a stent-valve for the aortic valve).

In some embodiments, the lower portion 16 has an extremity formed with a substantially zig-zag shape. The zig-zag shape may comprise lower apexes 16a and upper apexes 16b. The upper apexes 16b may be masked in FIG. 1 by the superimposed presentation of both the frontmost and rearmost cells of the lattice structure. The zig-zag shape may be substantially continuous around the circumference of the stent 12. The outer skirt 32 may have a peripheral edge having a zig-zag shape that matches substantially the zig-zag shape of the extremity of the lower portion 16. Such an arrangement can avoid excessive material at the extremity, and thereby facilitate crimping of the stent-valve 10. At the same time, the outer skirt 32 covers (for example, complete) open cells of the lattice structure down to the stent extremity to reduce risk of blood leakage through the apertures of the cells. The outer skirt 32 can also provide a layer of material over the struts of the stent, thereby to cushion the engagement between the stent and the sensitive native heart tissue.

The valve 14 may comprise biological tissue, for example, pericardium (such as porcine pericardium or bovine pericardium) or natural cardiac valve leaflets (for example, natural porcine cardiac valve leaflets, optionally attached to a portion of natural cardiac wall tissue). Other biological or non-biological material could also be used for the valve 14, as desired.

The stent 12 may optionally be of a self-expanding type that is compressible to the compressed configuration for loading into a delivery catheter 98 (FIG. 8) having a sheath 106 for constraining the stent 12 in the compressed configuration for delivery to the site of implantation. In use, by removal of the constraining effect of the sheath, the stent 12 self-expands to or towards the operative configuration. A self-expanding stent may, for example, be of shape-memory material, for example, shape-memory metal alloy, for example, nitinol. Alternatively, the stent 12 may be configured to be expanded by application of a foreshortening force from the delivery catheter and/or by application of expanding force from the delivery catheter, such as by using an expansion balloon.

The seal 40 may be configured for sealing against surrounding native tissue when the stent-valve 10 is implanted. In some embodiments, the seal 40 may be provided as an integral part of the stent-valve 10. Alternatively, in some embodiments, at least a component of the seal 40 may be provided as a separate item from the stent-valve. The stent-valve and at least one seal component may be provided and/or packaged together as a kit. The at least one component may, for example, be mountable to the stent-valve 10 prior to implantation, or it may be introduced (e.g. injected) into a portion of the stent-valve. The at least one component may be mounted/introduced as part of a pre-implantation preparation process (for example, described later).

The seal 40 may be arranged or arrangeable at any suitable position on the stent 12. In some embodiments, the seal 40 may be arranged between the upper crown portion 18 and the lower crown or tubular potion 16. In some embodiments, the seal 40 may be positioned optionally closer to the upper crown portion 18, alternatively optionally closer to the lower crown or tubular portion 16, alternatively optionally midway between the extremities of the two crown portions 16 and 18, alternatively optionally at a waist or trunk section between the two crown portions 16 and 18. In some embodiments, the seal 40 is carried on the exterior of the stent 12.

As mentioned above, in some embodiments, the (e.g. lower or inlet) periphery of the stent 12 has a substantially zig-zag shape. The zig-zag shape may comprise lower apexes 16a and upper apexes 16b. The upper apexes may be masked in FIG. 1 by the superimposed presentation of both the frontmost and rearmost cells of the lattice structure. The zig-zag shape may be substantially continuous around the circumference of the stent 12. The seal 40 may be arranged or arrangeable to be positioned only between the upper crown 18 and the upper apexes 16b. For example, the seal 40 does not extend to occupy space between the upper apexes 16b and the lower apexes 16a. Positioning the seal 40 clear of the lower apexes 16a can reduce the bulk of material at the extremity, and facilitate crimping. Additionally or alternatively, the seal may be positioned so as not to cover the upper crown 18. Leaving the upper crown 18 clear may enhance blood flow to coronary arteries (for example, in the case of a replacement valve for the aortic valve position).

Figure 2:
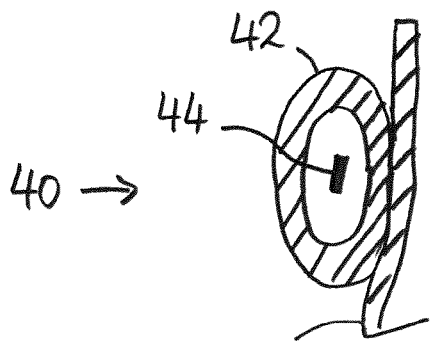
FIG. 2 is an enlarged schematic section showing the seal of FIG. 1 in isolation.

Referring to FIG. 2, the seal 40 may comprise a hollow sleeve/cuff 42 arranged to extend substantially in a circumferential direction around the stent 12, and containing swellable material 44 that swells when contacted by blood (or at least a blood component) to distend the hollow sleeve/cuff 42. The swellable material 44 may expand by absorbing blood or other liquids that contact the material 44. Such a seal 40 may initially be very compact in form, yet may expand significantly when contacted by blood, to fill gaps between the stent-valve 10 and any irregularities in the surrounding tissue. Examples of suitable swellable (e.g. absorptive) material 44 may be any of the hydrogels referred to in the aforementioned patents and applications: U.S. Pat. No. 5,769,882, EP 1262201, WO-A-2008/070442, US 2007/0060998, WO-A-2010/083558. The sleeve/cuff 42 may comprise flexible material. The sleeve/cuff 42 may comprise material that is elastically stretchable, and/or material that is substantially non-elastically-stretching.

In some embodiments, the swellable material 44 is provided in the form of, or comprises, beads. Use of beads may facilitate flow or migration of the swellable material within the seal 40, for example, during swelling or under the influence of swelling. This can enable the swellable material to be mobile in order to flow or migrate towards regions of free space or in which the seal is less confined, for example, corresponding to sites of potential leak paths around the exterior of the stent-valve 10.

Further details of the bead size (or the general size of particles of the swellable material 44 if not comprising beads) is discussed later.

In some embodiments, the hollow sleeve/cuff 42 or a wall or layer thereof, has or comprises an integral tubular structure. An integral tubular structure may mean that the sleeve/cuff (or wall or layer) 42 is produced as or comprises an original integral tube around an axis passing along a centerline of the tube; in the case of the sleeve/cuff 42 having or comprising a laminate structure, at least a structural substrate (e.g. substrate layer) within the laminate may be produced as an integral tube around an axis passing along a centerline of the tube. As used herein, references to the sleeve/cuff 42 having or comprising an integral tubular structure also apply to at least a wall or layer or a structural substrate of the laminate, whether or not mentioned explicitly, and whether or not the entire sleeve/cuff 42 may have such a structure. For example, integral tubular structures may be made by extrusion of the sleeve/cuff 42 material in tubular form, or by blow molding a preform to define a tubular form. Using an integral structure for the sleeve/cuff 42 may enable the sleeve/cuff 42 to achieve the otherwise conflicting requirements of desirably thin wall thickness, and good strength against bursting. Risk of bursting is often highest at join-lines of non-integral structures. Forming an integral tubular structure reduces the need for extensive join lines, in particular, a join line extending circumferentially around (and in some embodiments, substantially around) the prosthesis.

As illustrated later below, in some embodiments, an implantation method may include a step of (e.g., post-implantation) balloon-expansion of an implanted prosthesis stent-valve 10 carrying a seal 40. Providing the stent-valve 10 with a seal sleeve/cuff 42 having or comprising an integral tubular structure may be highly advantageous in enabling the seal sleeve/cuff 42 to made desirably thin, yet have good strength and resistance to bursting should the seal be subject to the high forces applied during (e.g. post-implantation) balloon-expansion, especially against the irregular or sharp contours of a calcified native anatomy.

Referring to FIG. 3, whether or not of an integral tubular structure, the material for the sleeve/cuff 42 may initially be provided in elongate tubular form 46 (FIG. 3a), for example, as an elongate integral tube. In some embodiments, (whether or not of an integral tubular structure) such an elongate tube 46 may be obtained from a balloon section of an inflatable cardiac valvuloplasty balloon 48 (FIG. 3b), for example, by cutting the balloon 46a near its ends, to extract an elongate tubular segment as the tube 46. Such balloon material already has desirable characteristics of being thin-walled yet strong to resist bursting when the balloon is inflated and bears directly against hard, irregular and sharp calcifications of a calcified vascular anatomy. The balloon material is also established as being bio-compatible and suitable for introduction into, and for direct contact with, the human vasculature.

Whether or not obtained from a cardiac valvuloplasty balloon, and whether or not having an integral tubular structure, example materials for the sleeve/cuff 42, or tube 46, may include one or more of: polyamide (PA), polyimide (PI), polyetheretherketone (PEEK), polyester (PE), for example, polyethylene terephthalate (PET).

Referring to FIG. 3c, in some embodiments using a seal 40 that is integral with the stent-valve 10, the elongate tube 46 may be attached to material 48, such as a material blank, for forming the outer skirt 32. The attachment of the tube 46 to the blank 48 is preferably by an attachment that does not puncture the elongate tube 46 for the sleeve/cuff 42. The tubular integrity of the tube 46 may be preserved. The attachment may, for example, be by fusion, or welding, or adhesive. In some embodiments, the blank 48 may be of the same material as the tube 46, to facilitate attachment, for example, by fusion. Creation of a sub-assembly 50 comprising both the seal sleeve/cuff 42 and the material 48 can facilitate easier handling during manufacture and production of the stent-valve 10.

Various techniques are possible. Purely by way of example, the material blank 48 may also be obtained from a section of a cardiac valvuloplasty balloon. Referring to FIG. 3d, the blank 48 may be manipulated while in tubular form. For example, mandrels 52 may be inserted into both the elongate tube 46 and the tubular blank 48. By a combination of heat and pressure (indicated by arrows 54), the tubes 46 and 48 may be fused together along an elongate line of attachment 56. Thereafter, the mandrels 52 are withdrawn, and the tubular blank 48 may be cut along a line 58 to define a planar section of material for the outer skirt 32.

To facilitate suturing the material 48 to the stent, the material 48 may alternatively be, or comprise, a fabric. For example, the material may comprise a film laminated to a fabric. The fabric may be laminated over the entire area of the film or merely in one or more zones intended to be sutured. The fabric may be easier than film to suture without risk of crack propagation. The presence of fabric in a laminate can also stabilize the laminate against crack propagation when a suture hole is made through the laminate. The fabric may be absent in the zone intended for, or substantially in register with the seal 40. The absence of fabric at this region may enable the material 48 to be thinner at the seal 40, to achieve a compact skirt and seal arrangement suitable for crimping.

Figure 3E:
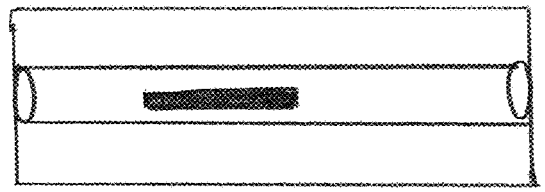
FIG. 3e is a schematic view illustrating insertion of swellable material into the sub-assembly of FIG. 3c.

Referring to FIG. 3e, and whether or not the tube 46 is a separate item, or attached to material 48 as sub-assembly 50, the swellable material 44 may be placed into the interior of the elongate tube 46. The swellable material 44 may be substantially smaller (e.g., shorter) than the tube 46, but be able to swell significantly upon contact with blood, to distend the sleeve/cuff 42 substantially around its periphery. The swellable material 44 may occupy only a portion of the circumferential length of the cuff, for example, optionally not more than about 75%, optionally not more than about 60%, optionally not more than about 50%, optionally not more than about 40%, optionally not more than about 30%, optionally not more than about 25%, optionally not more than about 20%. Optionally, the ends of the elongate tube 46 are each sealed to close the interior space of the tube 46 with the swellable material 44 captive therewithin. The ends may, for example, be sealed closed by welding, fusion, or adhesive.

Figure 3F:
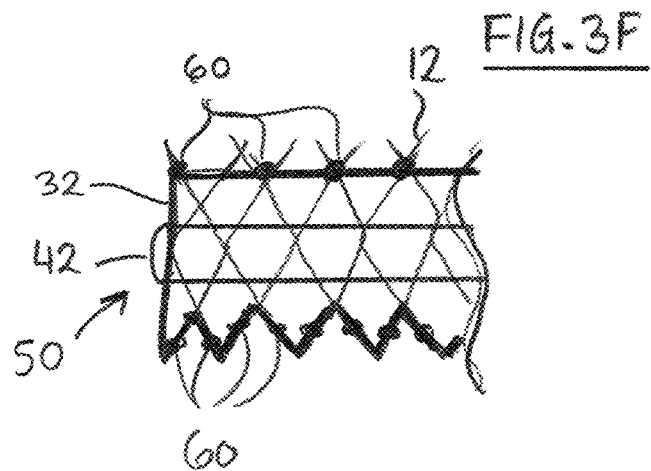
FIG. 3f is a schematic side view illustrating assembly of the sub-assembly to the stent of FIG. 1.
Figure 3G:
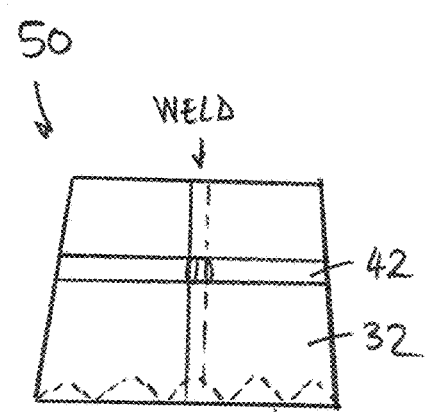
FIG. 3g is a schematic side view illustrating formation of a conical tubular sub-assembly for assembly to the stent of FIG. 1.

Referring to FIG. 3f, the sub-assembly 50 (if used) may be bent into a tubular form, and attached to the stent 12. In some embodiments, the sub-assembly 50 is attached to the stent in sheet form, by wrapping the sub-assembly 50 around the stent 12. Alternatively, (FIG. 3g), the sub-assembly may be first secured in a tubular form, and the tubular form attached to the stent 12. For example, the ends of the sub-assembly may be partly overlapped and welded together, to define a lapped join. The weld may seal closed the ends of the sleeve/cuff 42 (tubing 46). The weld may be clear of the swellable material within the sleeve/cuff 42. The tubular sub-assembly 50 may have a conical shape to match the contour of the lower portion of the stent 12. The tubular assembly 50 may have a zig-zag edge 50a to match the peripheral edge at one end (e.g. inlet end) of the stent. For example, the zig-zag edge 50a may be cut and/or trimmed after assembly to the stent 12.

In either case, the sub-assembly 50 may be secured to the stent 12 by sutures 60. Optionally, the sutures 60 pass only through the material of the outer skirt 32, and do not penetrate the material of the sleeve/cuff 42. The outer skirt 32 may act as the means for securing the sleeve/cuff 42 to the stent 12 without compromising the tubular integrity of the sleeve/cuff 42.

As can be seen in FIG. 3f, the elongate tube 46 is bent into a toroid shape around, or to match, the stent 12. The toroid shape may be a closed-loop toroid. Alternatively, the toroid shape may be partial loop, a split-loop, or a helical shape, for example. In some embodiments, the ends of the tube 46 are not sealed independently, but are sealed together to communicate with each other to define a circumferentially continuous hollow space across the join. However, in other embodiments, the ends of the tube 46 may be sealed closed to define a non-continuous interior across the join.

Figure 4:
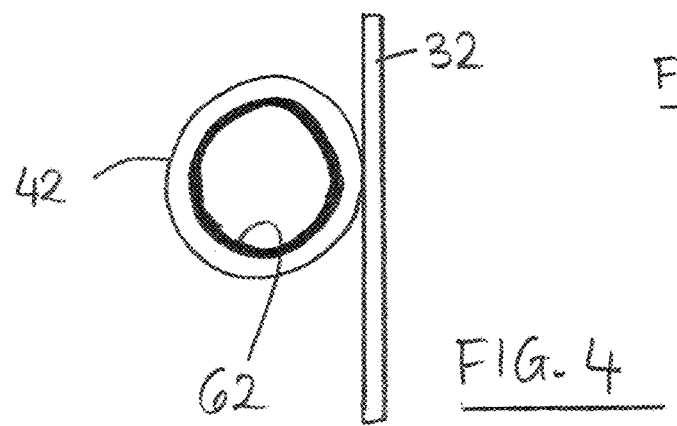
FIG. 4 is a schematic section illustrating a seal sleeve/cuff provided with a diffusion barrier layer according to some embodiments of the disclosure.

Referring to FIG. 4, the sleeve/cuff 42 may carry or comprise a diffusion barrier layer 62. For example, the sleeve/cuff material may comprise a laminate of (i) plastics film 64, and (ii) the diffusion barrier layer 62. The diffusion barrier layer 62 may serve to prevent diffusion of liquid, or other fluid, through the sleeve/cuff wall material. As explained later below, the stent-valve 10 may be immersed in liquid or other fluid during manufacture (e.g. during sterilization) and/or during storage when packaged ready for use. The diffusion barrier layer 62 can substantially prevent any trace of liquid diffusing through the sleeve/cuff wall, even though the plastics film 64 may be very thin.

In some embodiments, the diffusion barrier layer 62 is a metal or metal-compound. The diffusion barrier layer 62 may, for example, be deposited by plasma vapour deposition. The diffusion barrier layer 62 may have a thickness of less than 100 nm, optionally less than 50 nm, optionally less than 10 nm. The thickness of the diffusion barrier layer 62 may be exaggerated in FIG. 4. The diffusion barrier layer 62 may optionally be provided in a non-exterior-surface portion of the sleeve/cuff wall. For example, the diffusion barrier layer 62 may be provided on an interior face of the sleeve/cuff 42 (as shown in FIG. 4), or it may be provided as a non-surface portion of the laminate. Avoiding placing the diffusion barrier layer 62 on the exterior face of the sleeve/cuff 42 may reduce the risk of damage to the integrity of the diffusion barrier layer 62, for example, during subsequent handling and production of the stent-valve.

When the diffusion barrier layer 62 is formed on a sleeve/cuff 42 that has an integral tubular structure, plasma vapour deposition may, for example, be used to deposit the diffusion barrier layer in the hollow space of the sleeve/cuff 42, on the interior face of the sleeve/cuff 42. The diffusion barrier layer 62 may be deposited after the attachment of the sleeve/cuff 42 (or the tube 46) to the material 48 for the outer skirt 32, to avoid risk of damage to the diffusion barrier layer during attachment of the sleeve/cuff 42 or tube 46 to the material 48.

Alternatively, the exterior face of the sleeve/cuff 42 or tube 46 may be coated with the diffusion barrier layer material, and a further protective coating (not shown) applied over the exposed face of the diffusion barrier layer, to complete the laminate.

In either case, the tube 46 may act as a structural substrate of the resulting laminate, providing the integral tubular structure of the sleeve/cuff 42. Also, in either case, the diffusion barrier layer 62 may be an integral part of the stent-valve 10 that remains in place and is not removed at implantation.

Figure 5:
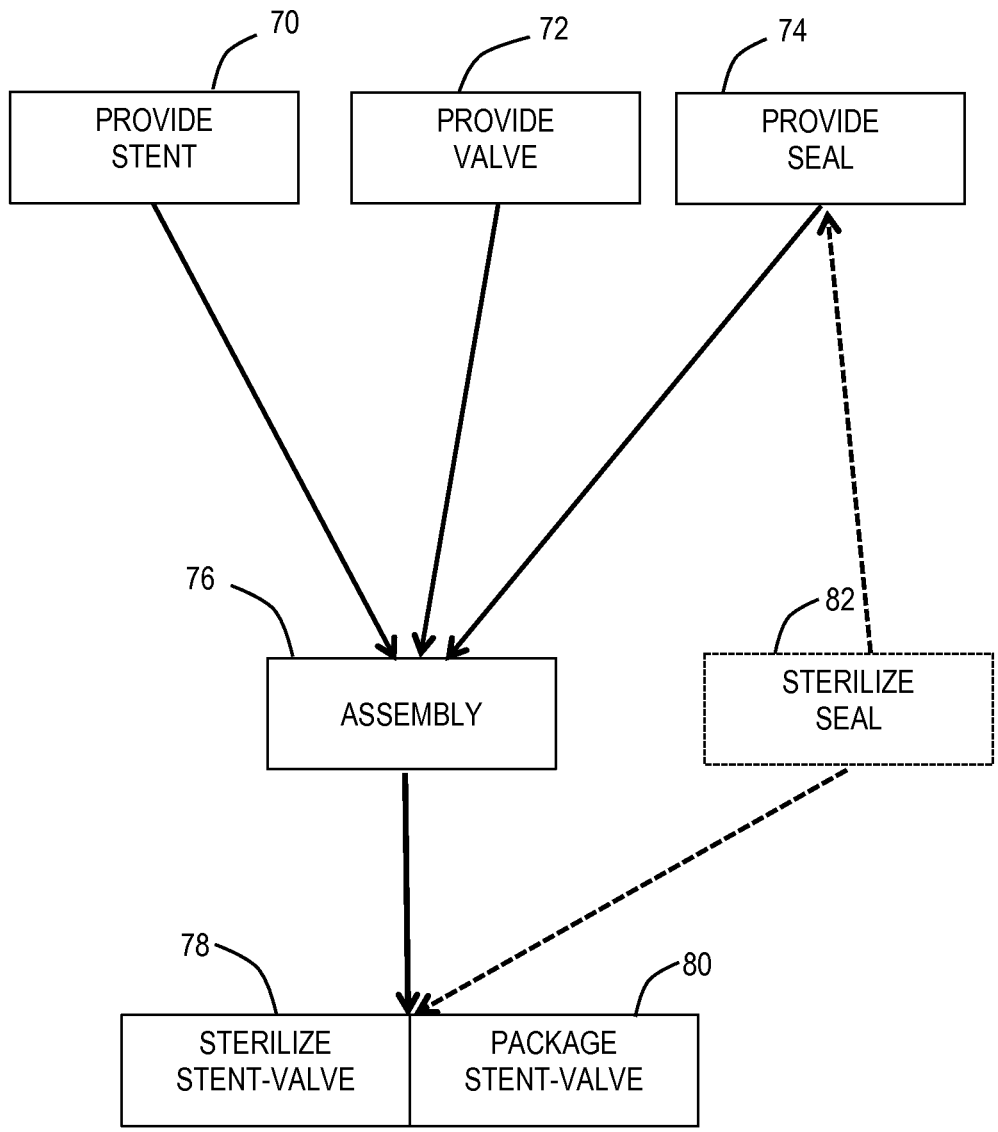
FIG. 5 is a schematic flow diagram illustrating steps of a method for producing a stent-valve according to some embodiments of the disclosure.

Referring to FIG. 5, a method of production of the stent-valve 10 may generally comprise one or more of the steps of:

Step 70: providing the stent 12;

Step 72: providing a prosthetic valve 14 (optionally attached to the inner skirt 30);

Step 74: providing the seal 40 (for example, the sub-assembly 50 including the sleeve/cuff 42 containing the swellable material, and optionally the material 48 for the outer skirt 32);

Step 76: assembling the valve 14 and the seal 40 to the stent 12, for example, using sutures to secure the valve 14 within the stent, and to secure the sub-assembly around an exterior portion of the stent 12. This step may be omitted during production if the seal 40 (or at least a component) is provided as a separate item from the stent-valve 10.

Step 78: sterilizing the assembled stent-valve 10;

Step 80: placing the assembled stent-valve 10 into packaging for storage; and Optionally step 82: sterilizing the seal 40 using a sterilization process different from step 78.

The step 78 of sterilizing the assembled stent-valve 10 may be performed by contacting the stent-valve 10 with a sterilization fluid, for sterilizing portions of the stent-valve contacted by the fluid. The fluid may, for example, be a liquid. Alternatively, the fluid may be a gas, or a liquid/gas combination. The sterilization fluid may be, or comprise a component, toxic to the human blood-stream. For example, the fluid may be intended to be rinsed or otherwise cleaned from the stent-valve prior to implantation. An example sterilization liquid comprises an aldehyde, for example, glutaraldehyde. The liquid may be an aqueous solution. Step 78 may optionally comprise heating the sterilization liquid to above room temperature, optionally above body temperature, optionally at least about 40° C., optionally at least about 50° C. Heating the sterilization liquid may enhance efficacy and/or speed of sterilization.

During step 78, the sleeve/cuff 42 prevents the sterilizing fluid from contaminating the swellable material 44, in the case that the seal 40 is integral with the stent-valve 10. As explained previously, the swellable material 44 may swell as a result of absorption of liquid. Toxic contamination of the swellable material 44 may make it difficult or impossible to remove the toxic liquid if chemically absorbed by the swellable material 44. Toxic contamination of the swellable material 44 may render the stent-valve less appropriate for implantation, and in some cases unimplantable. The sleeve/cuff 42 may prevent such contamination (for example, even if a sterilization liquid is heated). If used, the diffusion barrier layer 62 may further enhance the protective properties of the sleeve/cuff 42 in preventing any liquid from diffusing through the sleeve/cuff into the space used for the swellable material.

Steps 78 and 80 may be carried out in either order, or at least partly at the same time. For example, in some embodiments, at step 80, the stent-valve 10 may be placed into its final packaging and immersed in liquid. The stent-valve may be sterilized in its final packaging, using the same liquid. Such a technique may be referred to as "terminal sterilization". In other embodiments, the stent-valve 10 may be sterilized by immersion in a first liquid (step 78), and subsequently transferred to a second liquid or storage liquid (step 80). The storage liquid may be similar to the sterilization liquid, and may be or comprise a component that is toxic to the human blood stream. In such case, provision of the sleeve/cuff 42 (and optionally the diffusion barrier layer 62) protects the swellable material against toxic contamination. The stent-valve 10 may be stored in the storage liquid for an extended period of time. The sleeve/cuff 42 may be configured to resist penetration and/or diffusion of the storage liquid to the interior space of the cuff, for a period of at least 1 month, optionally at least 6 months, optionally at least 1 year.

Step 82 may be an optional separate step of sterilizing the seal 40, especially the interior of the sleeve/cuff 42. When a fluid-based sterilization technique may be used for step 78, such a technique should not be used for the interior of the seal 40 because, as explained above, it may result in contamination of the swellable material 44. Instead, in some embodiments, a different non-fluid-contact sterilization technique may be used, for example, using radiation sterilization. Step 82 may be carried out at any suitable stage of the production process. In some embodiments, step 82 may be carried out as part of step 74. For example, the sub-assembly 50 may be sterilized so that it is provided at step 74 with the sleeve/cuff 42 sterile (or at least having a sterile interior). Alternatively, step 82 may be carried out at any stage after step 76.

Figure 6:
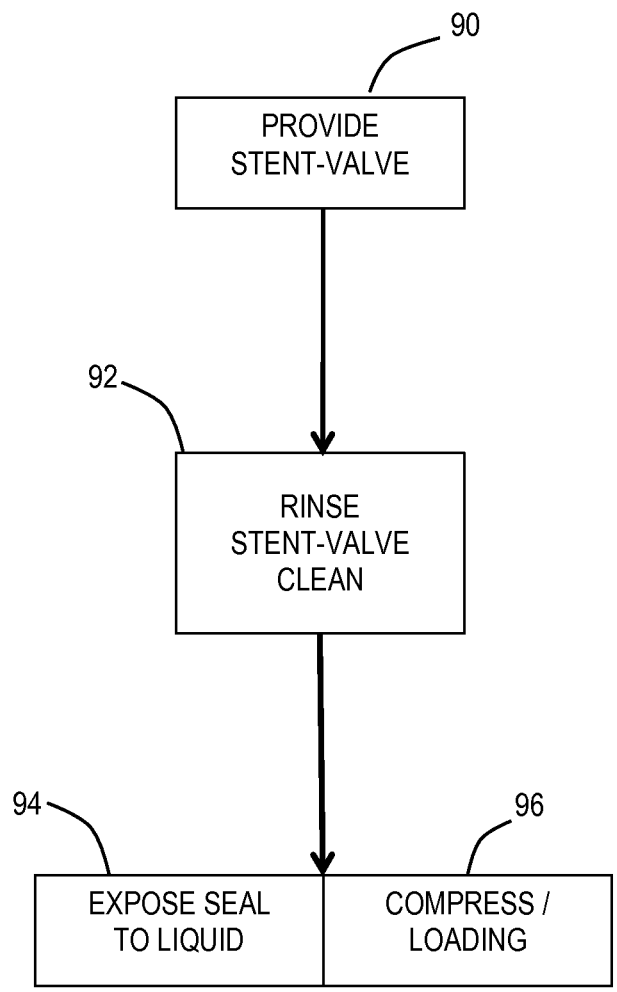
FIG. 6 is a schematic section illustrating steps of a method of preparing a stent-valve for implantation according to some embodiments of the disclosure.

Referring to FIG. 6, a method of preparing the stent-valve 10 ready for implantation may comprise one or more of the following steps (any of which, and optionally all of which, may be carried out outside the body of the patient to be implanted):

Step 90: providing the stent-valve 10 in a storage liquid, for example, as explained above;

Step 92: rinsing the stent-valve 10 to clean the storage liquid off the stent-valve 10. During step 92, the liquid-tight property of the sleeve/cuff 42 prevents liquid contact with the swellable material 44. This permits thorough rinsing of the stent-valve 10 desirable to remove substantially all of the storage liquid.

Figure 8:
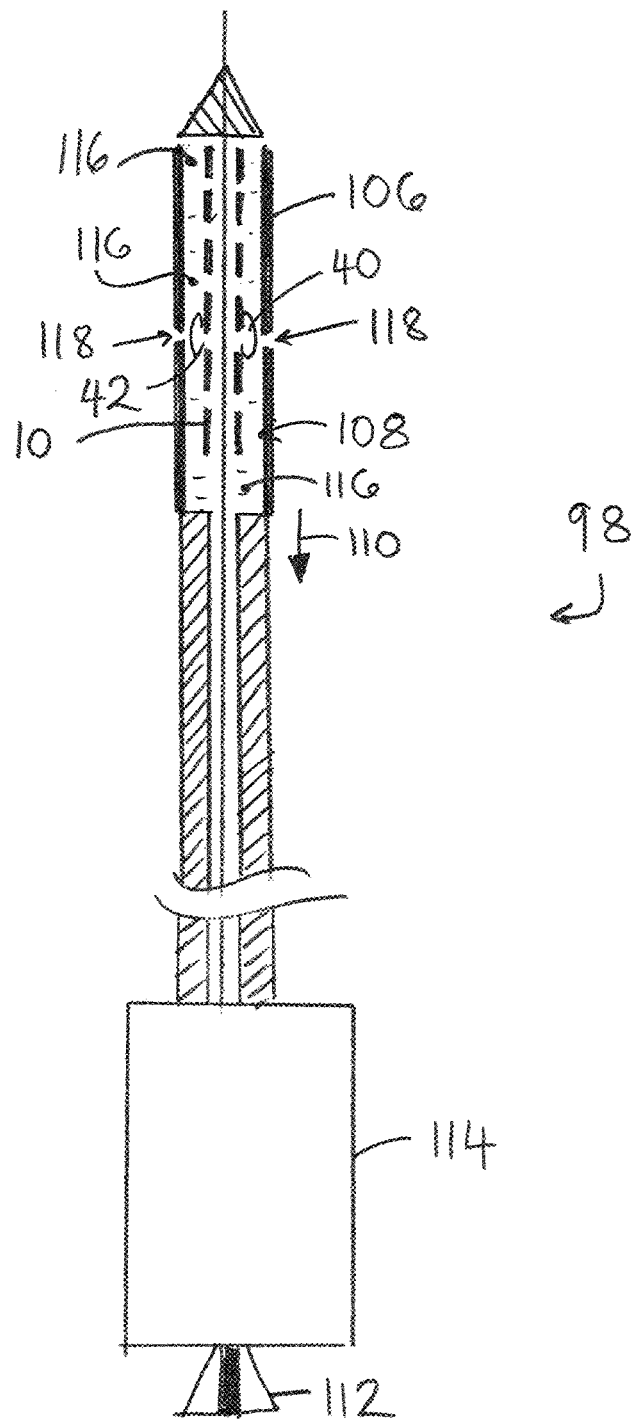
FIG. 8 is a schematic section of a first example of delivery catheter containing a stent-valve loaded therein according to some embodiments of the disclosure.

Step 94: after step 92, exposing the swellable material 44 to permit contact with liquid; and Step 96: after step 92, compressing the stent-valve 10 and/or loading the stent-valve 10 into a delivery apparatus 98 (FIG. 8).

Steps 94 and 96 may be carried out in either order or at least partly at the same time as each other.

Figure 7:
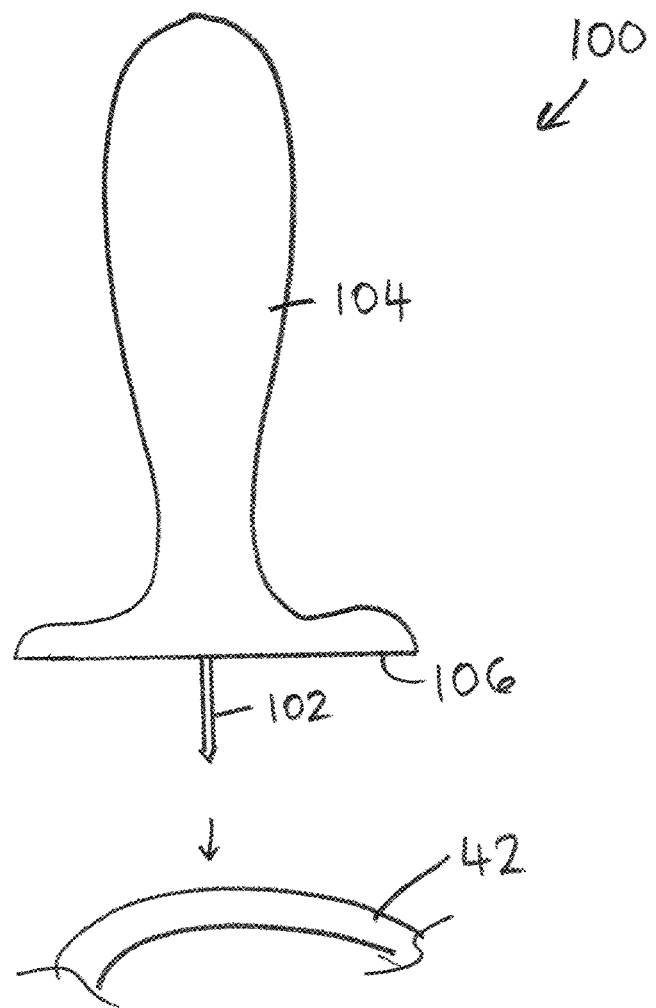
FIG. 7 is a schematic side view of a piercing tool for piercing a seal sleeve/cuff of a stent-valve according to some embodiments of the disclosure.

In some embodiments, step 96 may comprise the step of piercing the sleeve/cuff 42 using a piercing tool 100, to penetrate the sleeve/cuff material and create one or more liquid-admitting punctures in the sleeve/cuff 42. Piercing the sleeve/cuff 42 may leave the material of the sleeve/cuff 42 in place. For example, if used, a diffusion barrier layer may remain in place on the stent-valve 10, even after implantation. The punctures created in the sleeve/cuff 42 may pass through the diffusion barrier layer. An example piercing tool 100 is illustrated in FIG. 7. The piercing tool 100 may comprise at least one sharp pin 102 (or other sharp projection), and a handle portion 104 for enabling manual manipulation of the tool. The pin 102 may be dimensioned such that it can safely penetrate the sleeve/cuff 42 without reaching through to the interior of the stent 12, and valve 14. Damage to the valve 14 can be prevented. In some embodiments, a face or flange 106 of the handle portion 104 may act as an abutment that bears against the sleeve/cuff 42 surface to limit the depth of penetration, or another form of "stop" may be provided. In other embodiments, the piercing tool may comprise a roller having a surface on which is formed at least one sharp pin (preferably plural pins). In use, the roller is rolled on the surface to be pierced, and the punctures are created as the roller rotates on that surface.

Optionally, the step of piercing the sleeve/cuff 42 may include piercing the sleeve/cuff 42 at one or more positions that are clear of the location of the swellable material 44 within the cuff. Piercing the sleeve/cuff 42 away from the swellable material 44 may avoid risk of physical damage to a swellable material component. In some embodiments, the sleeve/cuff 42 may be transparent, or translucent, and the swellable material 44 may have a color (e.g. a distinctive color) to enable the location of the swellable material inside the sleeve/cuff 42 to be identified. This can help the medical practitioner if it is desired to pierce the sleeve/cuff 42 at positions clear of the location of the swellable material 44.

Additionally or alternatively, whether or not the sleeve/cuff 42 is to be pierced at positions clear of the swellable material 44, the sleeve/cuff 42 may comprise indicia to indicate suitable positions on the sleeve/cuff 42 at which to pierce/penetrate the sleeve/cuff material, to create the liquid-admitting punctures.

Generally, the ability to complete the exposure step 94 prior to introduction into the patient's body can avoid any need to rely on an exposure mechanism that is activated as part of the implantation procedure once inside the body, for example, the pressure responsive rupturing capsules described in the aforementioned US-A-2007/0060998 and WO-A-2010/083558. This can reduce the risk of complication should, in some cases, such an exposure mechanism malfunction and fail to operate correctly at the time of implantation and once already in the body, where the possibility of further intervention may already be limited.

In some embodiments, step 96 may comprise using a compressing tool (such as one or more funnel shaped tubes, not shown) through which the stent-valve 10 is advanced in order to compress the stent-valve 10 to its compressed configuration. The stent valve 10 may be coupled to, and/or loaded within a constraining sheath 106 of, the delivery catheter 98. The constraining sheath 106 may constrain the stent-valve 10 in the compressed configuration suitable for introduction into the patient via minimally invasive surgery or a percutaneous procedure.

In some embodiments, step 96 may be carried out at least partly while contacting the stent-valve 10 with liquid, for example, at least partly immersing the stent-valve in liquid. The liquid may be water or saline. The liquid may be cold, for example, at a temperature less than room temperature (for example, cold water or cold saline). For example, carrying out the compressing step in cold liquid may make the stent 12 more supple and easier to compress. Additionally or alternatively, the containment sheath 106 may be flushed or at least partly filled with liquid to purge air from the containment sheath 106, prior to introduction into a patient's body.

In some embodiments, especially where step 96 is carried out at least partly while contacting the stent-valve 10 with liquid, it may be decided to carry out step 94 after the stent-valve 10 (or at least a portion of the stent-valve 10 carrying the seal 40) is constrained in a compressed condition by the constraining sheath 106. Such a technique can (i) permit at least partial exposure of the swellable material 44 to liquid to at least partly wet or hydrate the swellable material 44 prior to introduction into the patient's body, and (ii) prevent the seal 40 from swelling prematurely, even though the swellable material 44 is exposed to liquid.

Wetting or hydrating the swellable material 44, at least partly, prior to introduction into the body may in some cases be beneficial to enable more efficient swelling of the material 44, and therefore of the seal 40 and/or sleeve/cuff 42, when the stent-valve 10 is implanted. It can avoid the need for the seal 40 to have to become wetted or to hydrate only on implantation. For example, speed of wetting and/or hydration and/or swelling may in some cases be a consideration if the liquid-admitting apertures (e.g. punctures) in the sleeve/cuff 42 are relatively small and/or if a relatively "slow" wetting and/or hydrating and/or swelling material 44 is used within the sleeve/cuff 42.

Additionally or alternatively, exposing the swellable material 44 only relatively late in the preparation procedure may combine (i) the advantage of being able to perform the exposure step 94 outside the patient's body (to avoid having to rely, as mentioned above, on an exposure mechanism that is activated as part of the implantation procedure once in the body), while (ii) limiting the amount of time during which the swellable material (44) is exposed to liquid prior to the implantation. Exposure during an excessive period of time might, in some cases and depending on the materials used, be counterproductive to the use as a dynamically swelling seal. In some embodiments, the swellable material 44 might be exposed to liquid outside the patient's body, for a time duration of: optionally not more than about 1 hour; optionally not more than about 30 minutes; optionally not more than about 20 minutes; optionally not more than about 15 minutes; optionally not more than about 10 minutes; optionally not more than about 9 minutes; optionally not more than about 8 minutes; optionally not more than about 7 minutes; optionally not more than about 6 minutes; optionally not more than about 5 minutes; optionally not more than about 4 minutes; optionally not more than about 3 minutes; optionally not more than about 2 minutes; optionally not more than about 1 minute.

FIG. 8 illustrates a portion of a delivery catheter 98, including a containment region 108 for the stent-valve 10 (indicated schematically in its compressed configuration by broken lines), and a constraining sheath 106. The delivery catheter 98 is illustrated in a condition optionally outside the patient's body, but in which the stent-valve 10 is loaded, and the delivery catheter 98 may be ready for introduction into the patient's body. The constraining sheath 106 may be translatable between a closed condition (as shown) in which the sheath 106 substantially constrains the stent-valve 10 in its compressed configuration, ready for introduction into the patient's body and delivery to the implantation site, and an open position (not shown) in which the sheath is translated in a direction (e.g. as illustrated by arrow 110 towards a handle portion 114, but optionally in the opposite direction away from the handle portion 114) to expose the stent-valve 10 for expansion to the operative configuration for implantation. The delivery catheter 98 may further comprise a flushing port 112 (which may optionally be at the handle portion 114 or handle-end of the delivery catheter). The flushing port 112 permits introduction of a liquid 116 (e.g. saline) for filling at least the containment region 108, and for purging trapped air from the containment region 108. The stent-valve 10 is immersed in the liquid 116 inside the containment sheath 106.

The sheath 106 may comprise a plurality of guide apertures 118 which, in the closed condition of the sheath 106, align with, or overlap or otherwise become in register with, the sleeve/cuff 42 and/or seal 40. The guide apertures 112 are intended to permit insertion of the pin 102 of the piercing tool 100, in order to create liquid-admitting punctures in the cuff, as described earlier above. The liquid-admitting punctures may be formed before, or after, or during, the introduction of liquid 116 into the containment region 108. The punctures may cause the liquid 116 to come into contact with the swellable material 44 of the seal 40. However, the constraining sheath 106 can prevent substantial expansion of the seal 40 until the moment of implantation.

Figure 9:
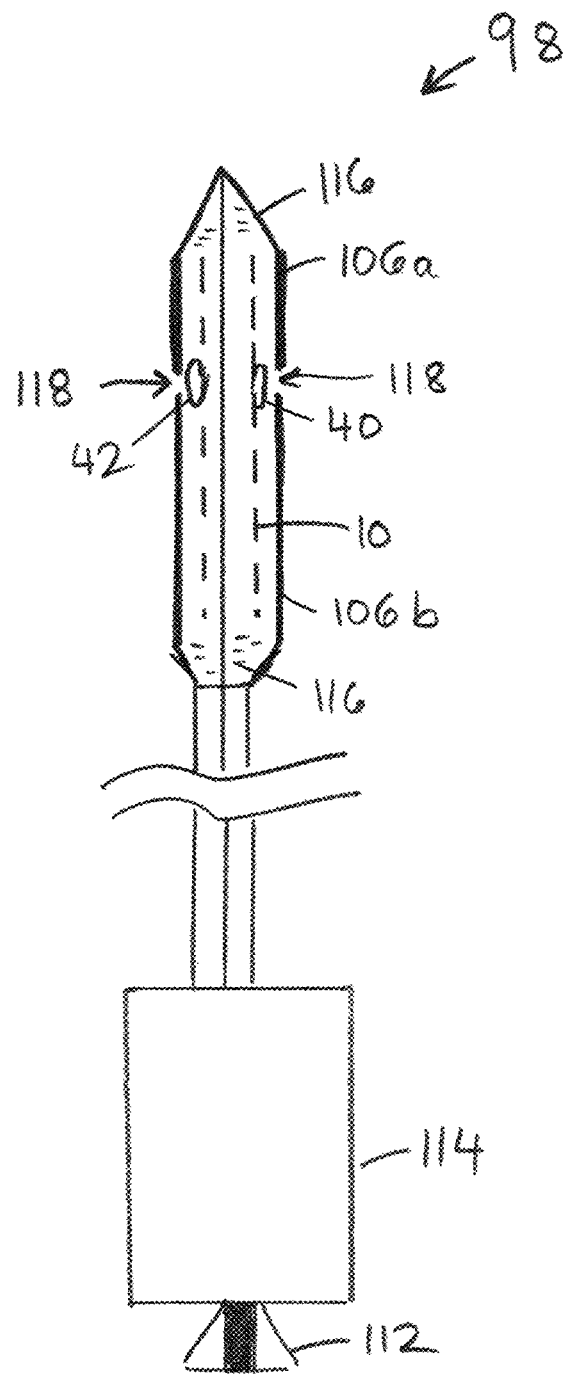
FIG. 9 is a schematic section of a second example of delivery catheter containing a stent-valve loaded therein according to some embodiments of the disclosure.

FIG. 9 illustrates an alternative version of the delivery catheter 98 comprising plural sheaths 106a and 106b. The sheaths may meet substantially end to end (as shown), or they may be at least partially overlapping (not shown). In a similar manner to that described above, at least one of the sheaths 106a and 106b may comprise guide apertures intended to permit insertion of the pin 102 of the piercing tool 100 to penetrate and pierce the sleeve/cuff 42 of the stent-valve 10. Alternatively (as shown), a small gap 118 at the interface between the two sheaths 106a and 106b may provide the guide aperture for insertion of the piercing tool.

Figure 10:
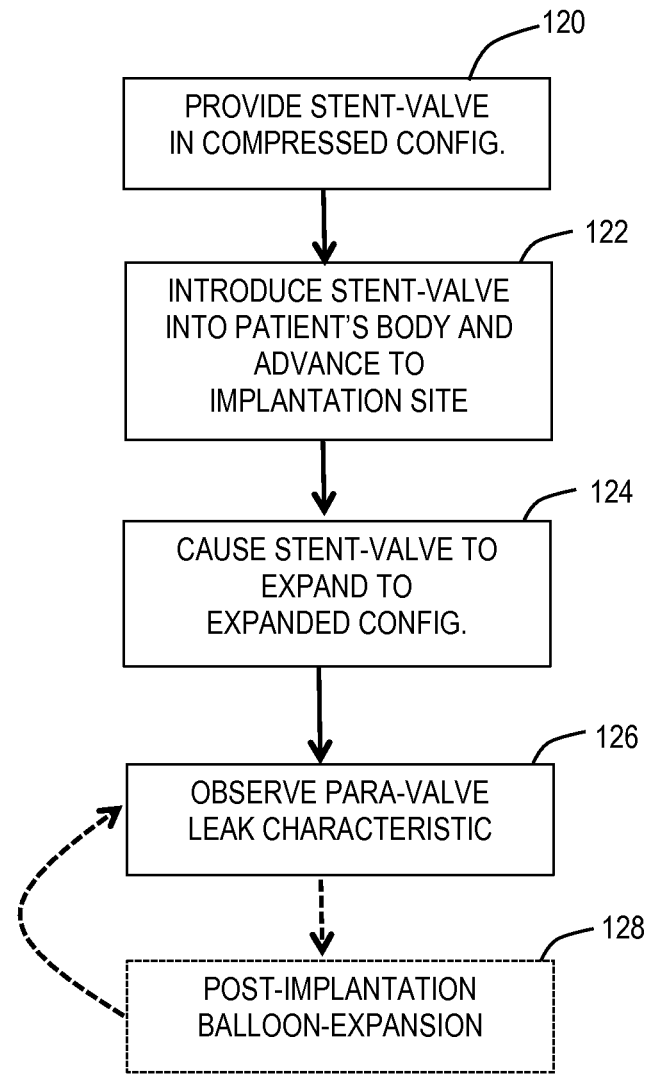
FIG. 10 is a schematic flow diagram illustrating steps of a method of implanting a stent-valve according to some embodiments of the disclosure.

Referring to FIG. 10, a method of implanting the stent-valve 10 may comprise one or more of the following steps:

Step 120: providing the stent-valve 10 in its compressed configuration ready for introduction into a patient's body. Optionally this step may include the preparation steps of FIG. 6 and/or apparatus of any of FIGS. 7 to 9;

Step 122: introducing the stent-valve 10 in its compressed configuration into the patient's body, and advancing the stent-valve 10 to a desired implantation site. By way of example, if the sleeve/cuff 42 may include a diffusion barrier layer 62, then step 122 may include introducing the stent-valve 10 with the diffusion barrier layer 62 still in place on the sleeve/cuff 42. Optionally, the sleeve/cuff 42 may have been pierced at once or more positions to create liquid-admitting punctures in the sleeve/cuff 42 that pass through the diffusion barrier layer 62.

Step 124: causing the stent-valve 10 to expand at the implantation site, from the compressed configuration to the operative configuration. If the stent 12 is of a self-expanding type, the expansion may be caused by removing a constraining sheath (e.g. sheath 106), in order to allow the stent 12 to self-expand towards the operative configuration. Additionally or alternatively, if the stent 12 is of a type in which manipulation of the stent-valve 10 is used to cause the stent-valve 10 to adopt its operative configuration, step 124 may include causing such manipulation, for example, by inflating an expansion balloon and/or foreshortening the stent 12 to a foreshortened state.

Step 126: observing one or more characteristics of the operative stent-valve. For example, one such characteristic may be the extent of para-valve leakage of blood. Such a characteristic may be observed using any suitable technique, for example, Doppler-effect ultrasound. Additionally or alternatively, the implantation position, and/or the extent to which the stent has expanded, and/or the pressure gradient through the valve, may be observed.

Step 128: in dependence of the result of the observation in step 126, performing post-implantation balloon expansion of the stent-valve 10. For example, if the observation of step 126 indicates that a para-valve leakage condition is not acceptable, and/or that the stent has not expanded as much as desired, and/or that the pressure gradient is undesirably high, a balloon catheter may be inserted into the interior of stent 12, and expanded to improve the seating/expansion of the stent 12 within the native anatomy at the implantation site. If the observation at step 126 indicates that a para-valve leakage condition and/or other conditions is acceptable (for example, there is no substantial leakage), then step 128 may be skipped.

Step 128 may be performed after a time interval sufficient to permit swelling of the seal 40 to adapt to the native anatomy. For example, the time interval may be at least about 30 seconds, optionally at least about 40 seconds, optionally at least about 50 seconds, optionally at least about 1 minute, optionally at least about 75 seconds, optionally at least about 90 seconds, optionally at least about 105 seconds, optionally at least about 2 minutes, optionally at least about two-and-a-half minutes, optionally at least about 3 minutes, optionally at least about three-and-a-half minutes, optionally at least about 4 minutes, optionally at least about four-and-a-half minutes, optionally at least about 5 minutes. Additionally or alternatively, the time interval may optionally be not substantially more than about 10 minutes, optionally not substantially more than about 9 minutes, optionally not substantially more than about 8 minutes, optionally not substantially more than about 7 minutes, optionally not substantially more than about 6 minutes, optionally not substantially more than about 5 minutes, optionally not substantially more than about 4 minutes, optionally not substantially more than about 3 minutes, optionally not substantially more than about 2 minutes, optionally not substantially more than about 1 minute.

It may not be intuitive to consider carrying out post-implantation balloon-expansion of a stent-valve that includes a swellable seal 40, because it might ordinarily be expected that the seal 40 will be able to seal against the anatomy automatically. However, steps 126 and 128 may permit the medical practitioner to determine, at least prior to completion of the medical procedure and while the patient is still in a condition ready for intervention, the efficacy of the seal 40 in sealing between the stent-valve 10 and the surrounding local anatomical tissue. If the seal 40 is determined not to be sufficiently effective, then step 128 may be used to increase the seating of the stent-valve 10 within the local anatomy, and the associated sealing effect of the seal 40. Steps 126 and 128 may be performed once, or repeated two or more times, as desired, for example, until para-valve leakage is reduced to an acceptable condition.

As explained earlier above, the seal 40 may be configured to be able to withstand a post-implantation balloon-expansion procedure, without risk of bursting.

Figure 11:
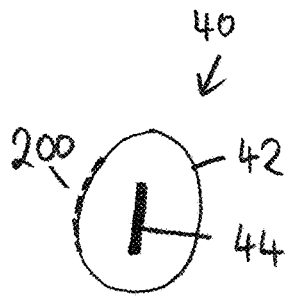
FIG. 11 is a schematic section through a further example of seal strip of integral tubular structure.
Figure 12:
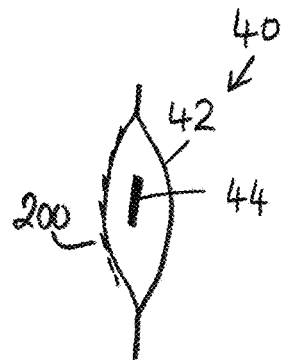
FIG. 12 is a schematic section through a further example of seal strip of envelope structure.

Referring to FIGS. 11 and 12, alternative structures of seal 40 are illustrated. The seal 42 comprises sleeve/cuff 42 containing swellable material 44. These embodiments may use any of the details described above for the sleeve/cuff 42 of preceding embodiments. In FIG. 11, the sleeve/cuff 42 may comprise an integral tubular structure, providing equivalent advantages to those discussed above. In FIG. 12, the sleeve/cuff 42 may comprise an envelope formed of one or more walls of material welded or otherwise secured together along one or more peripheries. For example, the envelope structure may be made of a single sheet that is folded and secured to itself around a common periphery, or multiple sheets (e.g. two sheets) welded or otherwise secured to each other around mutual peripheries.

However formed, the sleeve/cuff 42 may comprise a single wall, or the sleeve/cuff may comprise plural walls nested one behind, or within, another. At least one wall may comprise a single layer of material, and/or at least one wall may comprise plural layers of material (e.g. a multi-layered wall and/or a laminate).

The sleeve and/or cuff 42, or at least a wall or layer thereof, may comprise a region 200 that is permeable or at least semi-permeable to liquid. The permeable/semi-permeable region may be configured to (i) allow communication of blood components (or at least a blood component) therethrough (for example, into the interior of the sleeve/cuff 42 to cause the swellable material 44 to swell), and/or (ii) obstruct passage therethrough of blood emboli (for example, to substantially prevent escape into the blood stream of any emboli that may form within the sleeve/cuff 42), and/or (iii) obstruct passage therethrough of swellable material 44 particles (for example, to substantially prevent escape into the blood stream of any loose particles of the swellable material 44).

Figure 13:
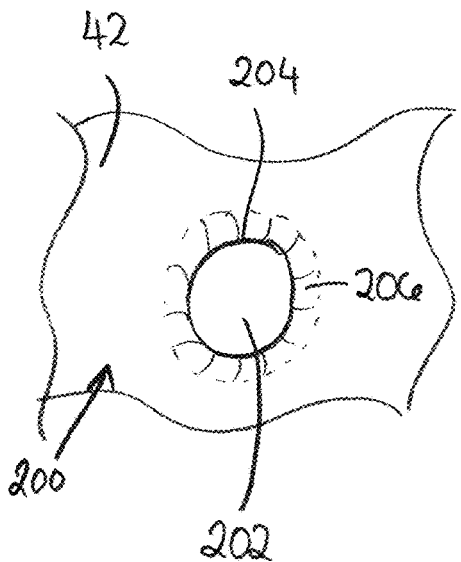
FIG. 13 is a schematic plan view, on enlarged scale, of a portion of a laser perforated sheet for use in the seal.

The permeable/semi-permeable region 200 may have pores (e.g. perforations 202 of FIG. 13). The pore size (e.g. average pore size) may, for example, be not substantially greater than about 0.2 mm. Optionally, the pore size may be not substantially greater than about 0.15 mm, optionally not substantially greater than about 0.12 mm, optionally not substantially greater than about 0.11 mm, optionally not substantially greater than about 0.1 mm, optionally about 0.1 mm, optionally not substantially greater than about 0.05 mm, optionally between about 0.05 mm and about 0.02 mm, optionally not substantially greater than about 0.01 mm, optionally not substantially greater than about 0.009 mm, optionally not substantially greater than about 0.008 mm, optionally not substantially greater than about 0.007 mm, optionally not substantially greater than about 0.006 mm, optionally not substantially greater than about 0.005 mm, optionally not substantially greater than about 0.004 mm, optionally not substantially greater than about 0.003 mm, optionally not substantially greater than about 0.002 mm, optionally not substantially greater than about 0.001 mm.

In some embodiments, the permeable/semi-permeable region 200 may extend over only a portion of the sleeve/cuff 42, and/or over only a portion of a wall of the sleeve/cuff 42, and/or a layer of the sleeve/cuff 42.

The permeable/semi-permeable region 200 may comprise perforated film, for example, laser perforated film.

The (e.g. laser) perforated film may be a monolayer film, or a laminate of two or more layers. The pore size of the (e.g. laser) perforated film may optionally have a variation of less than 20% from an average pore size, optionally less than 15% from an average pore size, optionally less than 10% from an average pore size, optionally less than 5% from an average pore size.

In some embodiments, the (e.g. laser) perforated film may have a thickness of not substantially greater than 0.05 mm. Use of such a thin film can contribute to achieving a compact sleeve/cuff 42 for enabling the stent-valve to achieve a desirably small size for delivery by catheterization. Optionally the film thickness is not substantially greater than about 0.045 mm, optionally not substantially greater than about 0.04 mm, optionally not substantially greater than about 0.035 mm, optionally not substantially greater than about 0.03 mm, optionally not substantially greater than about 0.025 mm, optionally not substantially greater than about 0.02 mm, optionally not substantially greater than about 0.015 mm, optionally not substantially greater than about 0.01 mm, optionally not substantially greater than about 0.005 mm. In some embodiments, the film thickness may be between about 0.005 mm and about 0.015 mm, optionally between about 0.005 mm and about 0.01 mm, and optionally between about 0.006 mm and about 0.008 mm, optionally about 0.007 mm.

In some embodiments, the (e.g. laser) perforated film may have a strength (e.g. linear tensile strength) at least 50% of the film strength prior to laser perforation, optionally at least 60% of the strength prior to laser perforation, optionally at least 70% of the strength prior to laser perforation, optionally at least 80% of the strength prior to laser perforation, optionally at least 90% of the strength prior to laser perforation. Such characteristics can contribute to a strong film even with thin film thickness.

Referring to FIG. 13, in some embodiments, the pores 202 (or at least a majority thereof) in the (e.g. laser) perforated film are substantially round and/or have a cauterized perimeter 204 and/or have a raised margin 206 around their perimeter. Such a feature or features may contribute individually or in combination to film strength even with thin film thickness. A round pore shape can avoid sharp corners in the peripheral shape that could be points of stress concentration or lead to outward crack propagation. Cauterization of the material around the perimeter 204 of the pore may also advantageously reduce risk of outward crack propagation. A raised margin 206 of material around the pore perimeter may also provide additional material, and hence strength, surrounding the open area of the pore.

Figure 14:
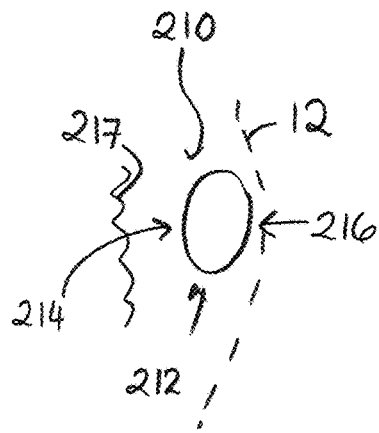
FIG. 14 is a schematic side view showing an interface between a stent, seal and native anatomy, and illustrating regions of blood flow to the seal.

Referring to FIG. 14, the permeable/semi-permeable region 200 may extend substantially over the entire surface of the sleeve/cuff 42, or the region 200 may be positioned in one or more specific zones, leaving other zones substantially non-perforated.

In some embodiments, the permeable/semi-permeable region may be disposed in one or more of:

A zone 210 facing substantially or at least partly towards the stent-valve blood outlet. When the valve 14 closes in use, blood back-pressure may tend to urge blood towards the seal 40 from the outlet direction, and placing the permeable region in zone 210 may provide good communication of blood to the seal for causing the swellable material 44 to swell; and/or A zone 212 facing substantially or at least partly towards the stent-valve blood flow inlet. Blood passing dynamically through the stent-valve generally approaches the stent-valve from the inlet direction, and placing the permeable region in zone 121 may provide good blood communication into the seal; and/or A zone 214 facing substantially or at least partly radially outwardly and/or a zone 216 facing substantially or at least partly radially inwardly.

In some embodiments in which at least a wall or layer of the cuff/sleeve 42 having the perforations is, in use, able to directly contact the surrounding native tissue, the permeable region may optionally be configured to be outside of the zone 214. Such an arrangement can avoid or reduce any risk that hard calcification 217 of the native tissue could enlarge a perforation by direct contact therewith, or otherwise damage the perforated region 200.

Figure 15:
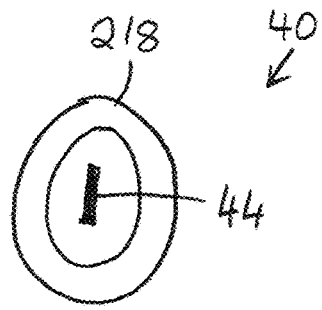
FIG. 15 is a schematic section through a further example of seal strip having multiple walls.

Referring to FIG. 15, in some embodiments, the cuff/sleeve 42 may further comprise an impermeable layer or wall 218 extending partly or entirely around the periphery of the cuff/sleeve 42 when viewed in cross-section, and/or partly or entirely in the circumferential direction of the stent-valve 10.

Referring to FIGS. 16-37, in some embodiments, at least a component of the seal 40 may be provided as a separate item from the stent-valve 10. The at least a component of the seal 40 and the stent-valve 10 may be provided and/or packaged together, for example, as a kit. The at least a component of the seal 40 may be intended to be mounted or fitted or introduced to the stent-valve 10 as part of a pre-implantation preparation process, e.g. after rinsing the stent-valve 10 clean of any storage solution. In the embodiments of FIGS. 16-29, the seal 40 is provided in a kit with a stent-valve, but as a separate or non-integral component, and is intended to be mounted to the stent-valve 10 as part of the pre-implantation preparation process. In the embodiments of FIGS. 31-37, a seal component 300 is provided in a kit with a stent-valve, but as a separate or non-integral component, and is intended to be mounted to the stent-valve as part of the pre-implantation process. The embodiments are described below initially in the form of a separate seal 40, but it will be appreciated that the same principles may be applied equally to a seal component 300. The term "seal component" may be interchanged for "seal" in any of the following description.

The seal 40 may comprise the swellable material 44 and optionally a cuff/sleeve 42. The cuff/sleeve 42 may comprise a permeable or semi-permeable region 200. The seal 40 may be generally elongate. The seal 40 may be provided in its own sterilized container 220, e.g. a pouch. The pouch may be a tear-open pouch. The seal 40 may have been sterilized using any suitable process, for example, radiation sterilization. The seal 40 may have been sterilized in its container 220.

In some embodiments, the stent-valve 10 comprises a dedicated (e.g. seal) accommodation region 221 to which the seal or seal component is mountable. The accommodation region 221 may be provided as part of an outer skirt 32 of the stent-valve 10.

Figure 17:
FIG. 17 is a schematic perspective view illustrating a discontinuous channel for accommodating a mountable seal.

The (e.g. seal) accommodation region 221 may be or comprise an (e.g. seal) accommodation channel 222. In some embodiments, the accommodation channel may be discontinuous. Referring to FIG. 17, a discontinuous channel 222 may be provided by a series of spaced apart loops 224, for example, similar to clothing belt loops. The number of loops 224, and the circumferential length of each loop 224, may be selected to provide a desired mark/space ratio (e.g. closed-area/open-area ratio). The mark/space ratio may optionally be about 1. Additionally or alternatively, the ratio may be less than 1, optionally less than about 0.75, optionally less than about 0.5, optionally less than about 0.25. Additionally or alternatively, the ratio may at least about 1, optionally at least about 1.25, optionally at least about 1.5, optionally at least about 1.75, optionally at least about 2, optionally at least about 2.5, optionally at least about 3.

Figure 18:
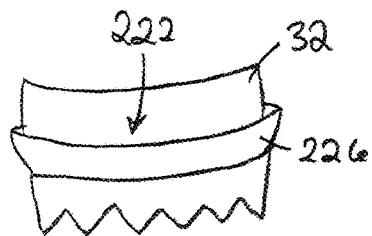
FIG. 18 is a schematic perspective view illustrating an open-side channel for accommodating a mountable seal.
Figure 19:
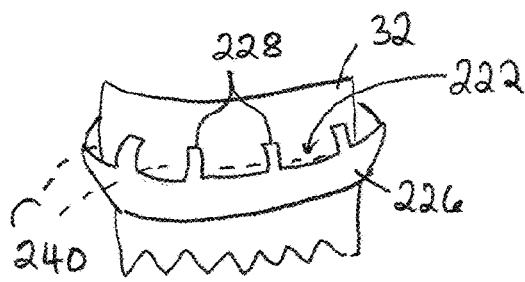
FIG. 19 is a schematic perspective view illustrating a first example of partly open channel for accommodating a mountable seal.
Figure 20:
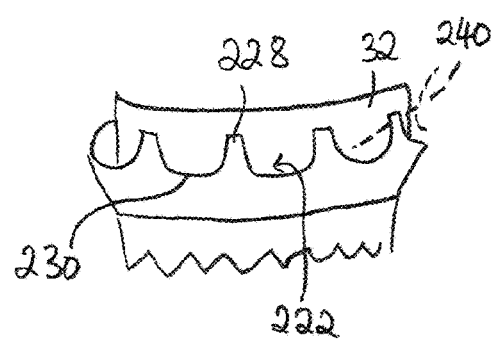
FIG. 20 is a schematic perspective view illustrating a second example of partly open channel for accommodating a mountable seal.

Referring to FIG. 18, a substantially continuous accommodation channel 222 may be provided by an (e.g. annular) flap 226 of material extending substantially continuously in a circumferential direction around the stent-valve 10. The flap 226 may define a channel that is open in one direction, for example, open in a direction facing towards the blood outlet end of the stent-valve in FIG. 18, and/or open in an opposite direction facing towards the blood inlet end of the stent-valve (not shown). Referring to FIG. 19, the flap 226 may further comprise a series of spaced apart extensions 228 that couple to the stent-valve, to define a series of clearances between adjacent extensions 228 instead of a continuously open region. The extensions 228 may define a castellated shape. Referring to FIG. 20, an edge 230 of the flap may have a scalloped shape between the extensions 228 to define a curved shape of the clearances thereby to avoid abrupt edges.

Figure 21:
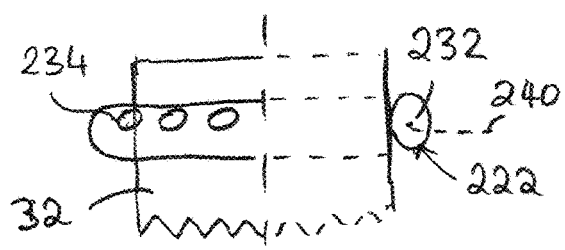
FIG. 21 is a schematic partial side view/partial section illustrating a tubular channel for accommodating a mountable seal.

Alternatively, referring to FIG. 21, a substantially continuous accommodation channel 222 may be provided by a tube (for example, an envelope) 232. The tube 232 may have an integral tubular structure, providing similar advantages to those described previously.

Additionally or alternatively, In some embodiments, the tube 232 may comprise permeable or semi-permeable material for admitting communication of blood (or at least a blood component) to the interior of the tube 232. For example, the material may be a fabric (for example, of PET, PEEK, or other plastics fibre(s)). The material may have an aperture size (e.g. pore size) of not substantially greater than about 0.2 mm, optionally not substantially greater than bout 0.15 mm, optionally not substantially greater than about 0.1 mm, optionally not substantially greater than about 0.05 mm, optionally between about 0.05 mm and about 0.02 mm.

Additionally or alternatively, the tube 232 may optionally have communication openings 234 for admitting blood to the interior of the channel. In the example shown, at least some of the openings 234 may be arranged facing substantially or at least partly towards the stent-valve blood outlet. When the valve 14 closes in use, blood back-pressure may tend to urge blood towards the seal 40 from the outlet direction, and such an arrangement of the openings may provide good communication of blood to the seal 40 for causing the swellable material 44 to swell. Additionally or alternatively, at least some of the openings 234 may be arranged (not shown) facing substantially or at least partly towards the stent-valve blood flow inlet. Blood passing dynamically through the stent-valve generally approaches the stent-valve from the inlet direction, and such an arrangement of the openings may provide good blood communication into the seal 40. Additionally or alternatively, at least some of the openings may arranged (not shown) facing substantially or at least partly radially outwardly and/or facing substantially or at least partly radially inwardly.

For similar reasons to those discussed previously in relation to FIG. 14, in some embodiments, the openings 234 may be arranged so as not to face substantially radially outwardly. In other words, the radially outward facing portion of the tube 232 may have a substantially continuous surface to shield the seal 40 within the tube 232 from direct contact with hard calcifications of the surrounding native anatomy.

The seal 40 may be loadable or introducible into the channel 222 by any suitable means. In some embodiments, a loading filament 240 (e.g. made of medical suture thread) may be pre-laid within the channel 222 along a predefined path, and used as device for pulling or drawing the seal 40 into the channel 222. For example, the opposite ends of the thread 240 may project outwardly from the channel, for example through openings or clearances previously described, or through additional and/or dedicated loading apertures (not shown). In order to load the seal 40, one end of the filament 240 may be coupled to an end of the seal 40. Pulling on the opposite end of the filament 240 withdraws the filament 240 progressively from the channel, at the same time drawing the seal 40 into the channel along the predefined path previously occupied by the filament. The predefined path may extend at least partly circumferentially around the periphery of the stent-valve, along a path length corresponding to at least about 180 degrees, optionally at least about 225 degrees, optionally at least about 270 degrees, optionally at least about 315 degrees, optionally about or at least about 360 degrees. 360 degrees corresponds to a complete circumferential path length around the circumference of the stent-valve. The path length may optionally be greater, and correspond, for example, to about or at least about 1.5 turns, or optionally to about or at least about 2 turns, or more. Once the seal 40 is loaded, the filament 240 (or at least a projecting portion of the filament 240) may be disconnected (e.g. cut) from the seal 40 to leave the seal in place within the channel 222.

Figure 22:
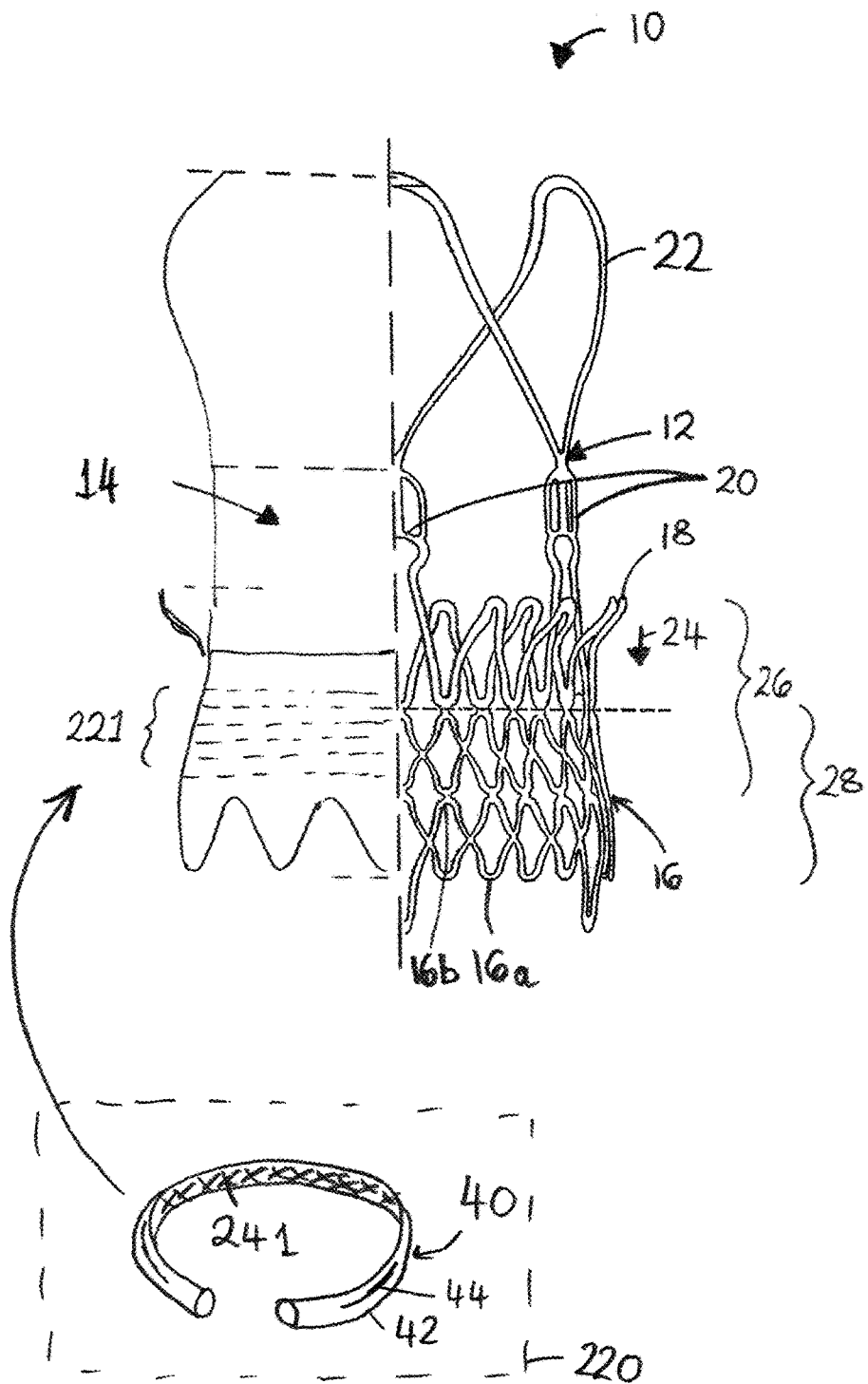
FIG. 22 is a is a schematic partial section similar to FIG. 1, but showing a seal as a separate component adhesively mountable to the stent-valve.

Alternatively, referring to FIG. 22, the seal 40 may be adhesively attachable to the stent-valve 10. For example, at least one of the seal 40 and the seal accommodation region 221 may comprise an adhesive region, optionally protected by a respective peelable release sheet. If adhesive is provided on only one part (e.g. on the seal 40), the other part (e.g. the seal accommodation region 221) may comprise a landing surface for adhesive attachment by the other part.

Alternatively, referring to FIG. 23, the outer skirt 32 may comprise a hollow band 242 into which the swellable material 44 may be introduced in flowable form, as part of the pre-implantation preparation process. An example flowable swellable material may, for example, be or comprise swellable beads, such as microspheres, for example, poly (vinyl alcohol-sodium acrylate) copolymer microspheres. In some embodiments, the flowable material may be injected into the band 242, either directly through the wall of the band, or using a dedicated inlet port 244. The band 242 may represent or correspond to a seal accommodation region 221 and/or a seal accommodation channel 222 in any of the following description.

As mentioned earlier, the concept of swellable material 44 provided in the form of, or comprising, beads may also be used whether the swellable material 44 is injectable, or whether the swellable material is pre-loaded into a sleeve/cuff.

The size of beads of swellable material (or a size of swellable material particles if not in bead form) may be chosen as desired. In some embodiments, the bead/particle size may be chosen according to one or more (and optionally all) of the following criteria:

In some embodiments, the bead/particle size prior to swelling (e.g. prior to hydration), may correspond to a transverse dimension (e.g. diameter) of at least about 0.005 mm, optionally at least about 0.01 mm, optionally at least about 0.02 mm optionally at least about 0.03 mm, optionally at least about 0.05 mm, optionally at least about 0.06 mm, optionally at least about 0.07 mm, optionally at least about 0.08 mm, optionally at least about 0.09 mm. Optionally, at least a majority of the beads/particles may have a size as defined, optionally at least 75% of the particles, and optionally substantially all of the particles.

Additionally or alternatively, the bead/particle size prior to swelling may correspond to a transverse dimension (e.g. diameter) that is greater than an aperture size (e.g. pore size) of a semi-permeable material forming at least a portion of a container for containing the beads/particles. Such an arrangement can be effective in obstructing escape of the beads from the seal. The transverse dimension of the beads may optionally be at least 1.5 times the aperture size, optionally at least double the aperture size, optionally at least three times the aperture size. Optionally, at least a majority of the beads/particles may have a size as defined, optionally at least 75% of the particles, and optionally substantially all of the particles.

Additionally or alternatively, the bead/particle size after swelling (e.g. after hydration), may correspond to a transverse dimension (e.g. diameter) of not substantially greater than about 0.1 mm, optionally not substantially greater than about 0.09 mm, optionally not substantially greater than about 0.08 mm, optionally not substantially greater than about 0.07 mm. With such a size constraint, even should particles escape from the confines of the seal, and enter the blood stream, it is believed that the particles are small enough not to present any significant embolism risk for the patient. Optionally, at least a majority of the beads/particles may have a size as defined, optionally at least 75% of the particles, and optionally substantially all of the particles.

Additionally or alternatively, the swellable material may have a swelling capacity to enable an increase in volume of at least about 64 times its dehydrated volume. The volume swelling factor may be represented by an equilibrium swelling volume ratio "qv" of at least about 64. In some embodiments, qv may be in the range of about 64 to about 216. A qv value of 64 may correspond to a linear swelling change of 4. A qv value of 216 may correspond to a linear swelling change of 6

In some embodiments, a combination of the above criteria may be used to define a bead/particle size prior to swelling of at least about 0.01 mm, a size after swelling of not substantially greater than about 0.09 mm, and pre-loaded or loadable (e.g. injectable) into a containment sleeve/cuff. At least a semi-permeable region of the sleeve/cuff may have a pore-size of not substantially greater than about 0.005 mm (for example, about 0.004 mm or less).

Whether or not the particle/bead size is chosen as above, the beads of swellable material 44 may optionally be free-floating within the seal 40 (especially but not limited to when injected in flowable form). Alternatively, referring to FIG. 31, in some embodiments in which the beads are pre-loaded into the seal 40, the beads may be optionally be organized into an elongate strip form 300. The strip 300 may optionally comprise at least one carrier sheet 302 (optionally two or more sheets) to provide a support and/or confining surface. For example, two sheets 302 may sandwich the beads 304 on either side. Such a strip may be easier to handle during manufacture than loose or free-floating beads 304. At the same time, the bead form of the material within the strip 40 may provide the same or similar enhanced mobility of the swellable material within the seal 40, for example, upon swelling.

Figure 16:
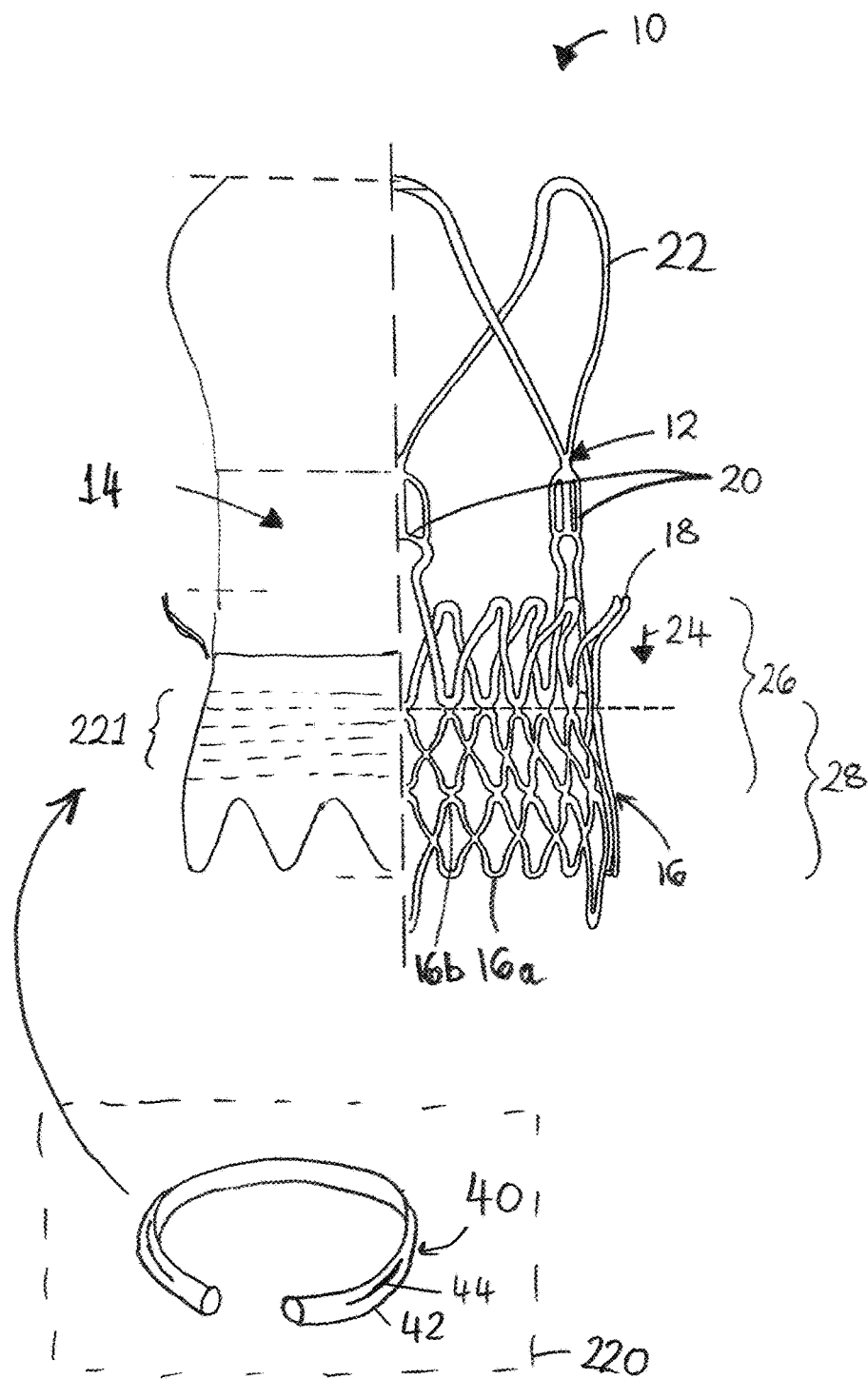
FIG. 16 is a schematic partial section similar to FIG. 1, but showing a seal as a separate component mountable to the stent-valve.

Referring to FIG. 16, if the stent geometry previously described for FIG. 1 is used, the seal accommodation region 221 (e.g. seal accommodation channel 222) may optionally be positioned to be clear of the upper crown 18 in order not to interfere with blood through the upper crown to coronary arteries (e.g. in the case of a stent-valve for the aortic valve position).

Additionally or alternatively, if the stent geometry previously described for FIG. 1 is used (referring also FIG. 16), the seal accommodation region 221 (e.g. seal accommodation channel 222) may be positioned only between the upper crown 18 and the upper apexes 16b of the lower and/or inlet extremity. For example, the seal accommodation region 221 does not extend to occupy space between the upper apexes 16b and the lower apexes 16a of the extremity. Positioning the seal 40 clear of the lower apexes 16a can reduce the bulk of material at the lower/inlet extremity of the stent, and facilitate crimping.

Referring to FIGS. 16 and 24, the outer skirt 32 may comprise at least one attachment zone 250 positioned axially above and/or below the seal accommodation region 221. The skirt 32 may be secured to the stent 12 and/or to the inner skirt 30 by the at least one attachment zone 250, such that the attachment does not interfere with, or increase the thickness of, the seal accommodation region 221. The skirt 32 may be attached by any suitable means, for example, suturing, welding, fusion or adhesive. In FIG. 16, suturing is indicating by a broken line. In some embodiments, two attachment zones 250 are provided, one above and one below the seal accommodation region 221. The lower periphery of the outer skirt 32 (and optionally of one of the attachment zones 250), may have a zig-zag shape to match a zig-zag shape of a lower and/or inlet extremity of the lower portion of the stent 12.

Referring to FIG. 25, the outer skirt may comprise a sheet of film material 252. The film material 252 may provide both the at least one attachment zone 250, and a support for or at the seal accommodation region 221, (indicated schematically in FIGS. 25-28). Alternatively, referring to FIGS. 26-28, the outer skirt 32 may comprise fabric material 254 at least at the one or more attachment zones 250. Fabric material may be easier to attach by means of suturing, with less risk to the integrity of the material than if a film is sutured. A polymer film material, and especially a crystalline polymer film material (such as PEEK, for example), may be vulnerable to outward crack propagation from suture holes, whereas a fabric made of the same material may much less vulnerable. FIG. 26 illustrates a hybrid skirt that comprises only fabric 254 for the attachment zones 250, and only film 252 at the seal accommodation region 221. The fabric and film regions may be welded together, for example. FIG. 27 illustrates a modified hybrid skirt in which the film 252 extends substantially the entire axial height of the skirt, and fabric material 254 is laminated at the attachment zones 250. The fabric material 254 can support the film 252 to provide resistance to crack propagation. The fabric material 254 may be heat sealed or fused to the film in order to form the laminate. FIG. 28 illustrates a further modified hybrid skirt in which the fabric and film are substantially coextensive and form a skirt consisting of laminate over substantially its entire axial height.

Referring to FIG. 29, a further example of separate seal 40 is illustrated. The seal 40 comprises a saddle or harness 258 that is clipped and/or hooked and/or threaded to the stent 12, for example, by attaching to the projecting apexes or valleys of the upper crown 18 and lower portion or crown 16.

Figure 31:
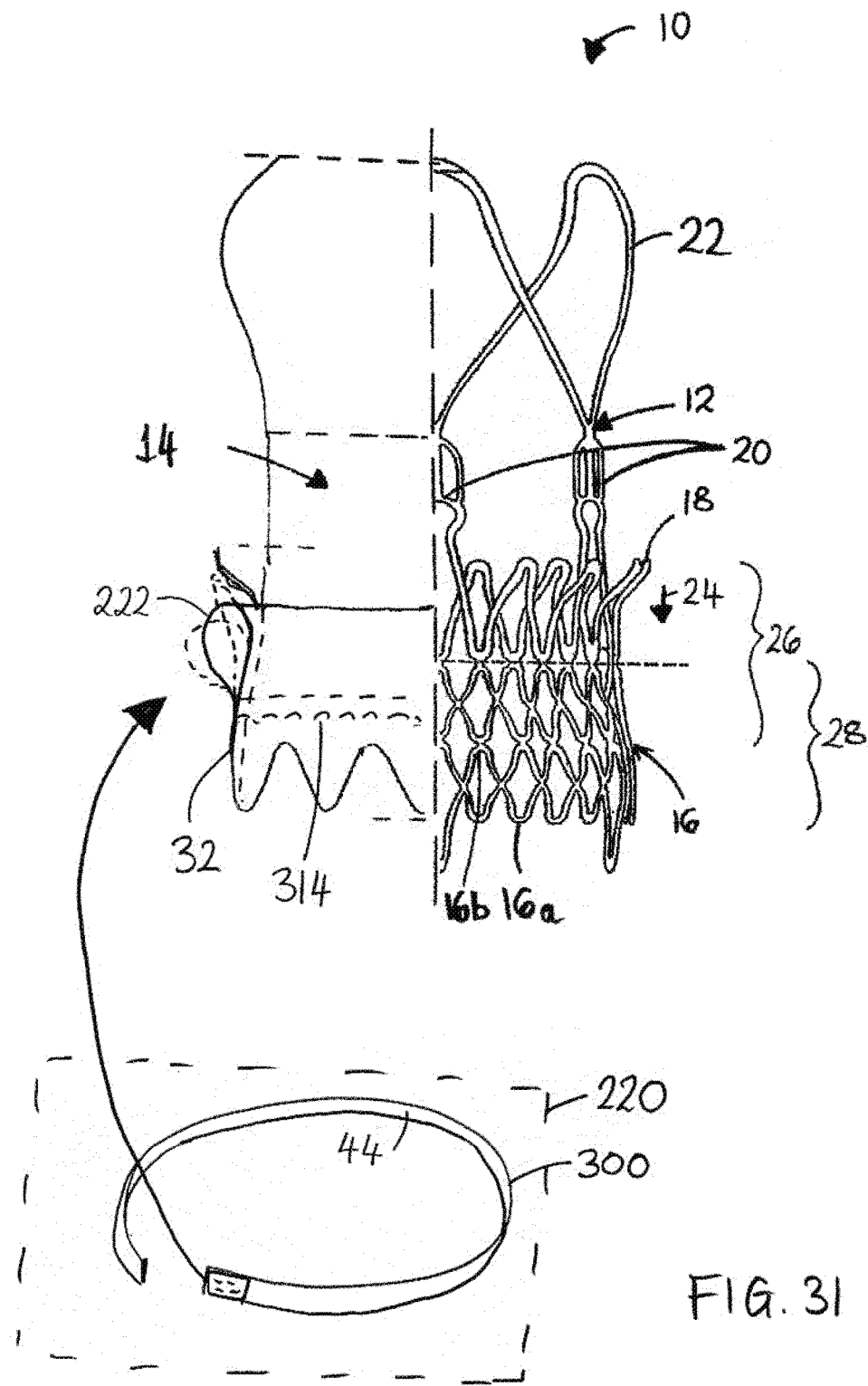
FIG. 31 is a schematic partial section similar to FIG. 1, but showing an alternative technique for mounting a seal component.
Figure 36:
FIG. 36 is a schematic cross-section through an example of seal component.

Referring to FIG. 31, a further example using a separate seal component 300 is illustrated. The seal component 300 comprises a strip of swellable material 44. Referring to FIG. 36, in some embodiments the swellable material may form a self-supporting strip without a substrate or backing Referring to FIG. 37, in other embodiments, the swellable material 44 may be supported by a backing layer or substrate 302 forming an integral part of the component 300.

In some embodiments, the seal component 300 may be absent a surrounding sleeve/cuff. Instead, the accommodation channel 222 described later may itself define an enclosing sleeve/cuff structure for the seal component 300 once the seal component has been loaded into the accommodation channel 222.

The seal component 300 may be packaged within its own sterilized container 220, e.g. a removable pouch or sleeve. The container 220 may be of a tear-open type. The component 300 may have been sterilized using any suitable process, for radiation sterilization. The component 300 my have been sterilized in its container 220.

In some embodiments, the accommodation channel 222 may be integral with a skirt 32 of the stent-valve.

Figure 32:
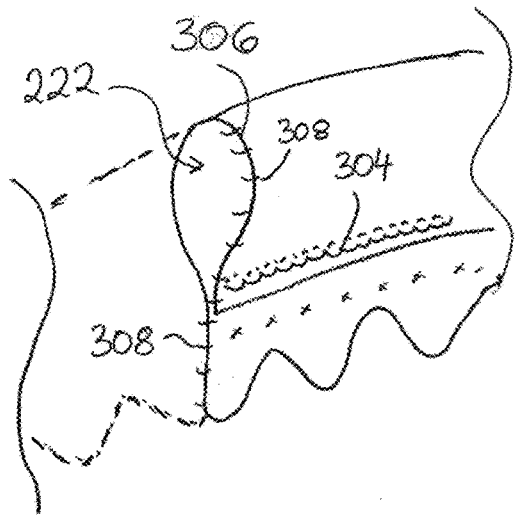
FIG. 32 is a schematic perspective view showing a technique for forming the skirt with accommodation channel.

Referring to FIG. 32, in some embodiments, the accommodation channel 222 may be formed by folding over a portion of permeable or semi-permeable material to define an envelope structure defining the channel 222. The folded over portion may be attached to the material wall, for example, by a line of stitching 304 (e.g. in the case of fabric material), of by a weld line (e.g. in the case of plastics film material). When stitching is used, the stitching may optionally be a single line of stitching alternating on either side of the material, or it may be a double line of stitches. For example, a double line of stitches may including a first line of stitching alternating on either side of the material, and a second line of stitches superimposed on the first line to pass generally through the same stitch holes as the first line, but alternating to extend on an opposite side of the material to the first line of stitching. Such a double line of stitches may provide a highly effective joint able to prevent leakage of the swellable material 44 therepast.

The material of the skirt 32 and/or accommodation channel 32 may, for example, comprise one or more of a fabric or an apertured film (e.g. laser-formed apertures), having a characteristic generally suitable for allowing blood (or at least a blood component to which the swellable material is response) into the interior of the accommodation channel, and/or generally confining the swellable material to the channel interior. Such characteristics may be similar to those already described previously.

In some embodiments, the folded over portion of the wall material may be at an inwardly facing surface of the skirt. This can provide a smoother and/or more continuous exterior surface for sealing against surrounding native anatomy.

In some embodiments, the skirt is formed from sheet material by folding over and attaching a portion of the material wall as described above. Thereafter the material may be bent into an annular and/or torroid shape, similar to the structure of FIG. 3G. The ends 306 of material may be joined together by any suitable fixing technique, including stitching and/or welding, as already described above.

In some embodiments, the ends 306 of material are joined together along the inner face (indicated by stitches 308), leaving the outwardly facing edges unfastened to define a loading aperture 310 for the channel 222. As described later, the loading aperture 310 may be closed by a closure after loading of the seal component 300. For example, a purse-string stitch 312 may be placed loosely so that it does not obstruct loading, and can be pulled tight later. The purse-string stitch 312 may be shown only in FIG. 35, to avoid obscuring the other drawings.

In some embodiments, a loading filament is also 240 is also laid within the channel 222, such that the opposite ends 240*a* and 240*b* cross each other at, and extend outwardly through, the loading aperture 310.

In some embodiments, the skirt 32 with the accommodation channel 222 is sutured to the stent at one or more suture lines 314 (FIG. 31) positioned below the channel 222. Such an arrangement allows the channel 222 to "float" relative to the stent, and extend to a height depending on the degree of distention of the channel (as indicated by the broken lines in FIG. 31). For example, prior to swelling of the seal, the channel 222 can be relatively flat, and may extend to partly cover the upper crown of the stent. However, in use, when the seal swells, the channel 222 will bulge outwardly and downwardly, such that the upper crown is no longer occluded.

Figure 33:
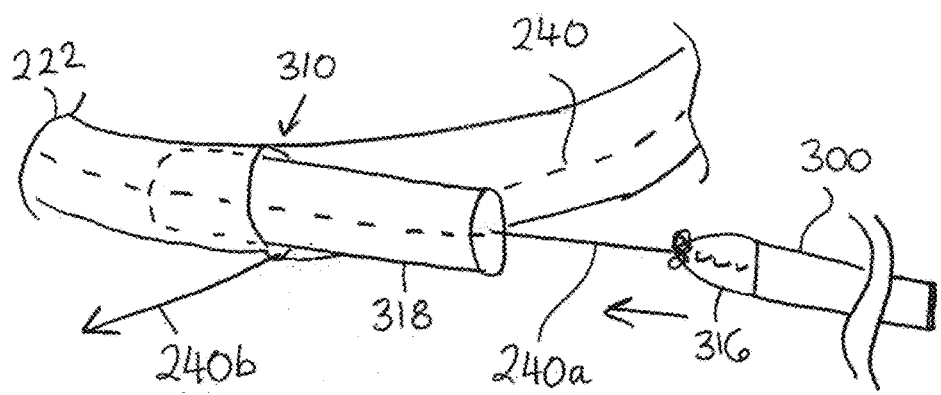
FIG. 33 is a schematic perspective view showing use of an introducer sheath for facilitating initial loading of the seal component.

Referring to FIG. 33, in use to load the sealing component 300 into the channel, one end 240*a* of the loading filament is attached to the component 300. For example, the end 240 of the filament 240 may be stitched to and/or knotted to the component 300. The tip of the component 300 may be reinforced with additional material 316, such as fabric, to distribute the load and avoid accidental tearing at the tip.

In some embodiments, an introducer tube 318 may be used to facilitate smooth entry of the component 300 into the channel. The introducer tube 318 may be inserted partly into the loading aperture 310 of the channel 222. The introducer tube 318 may be made of any suitable smooth and/or flexible plastics.

Figure 34:
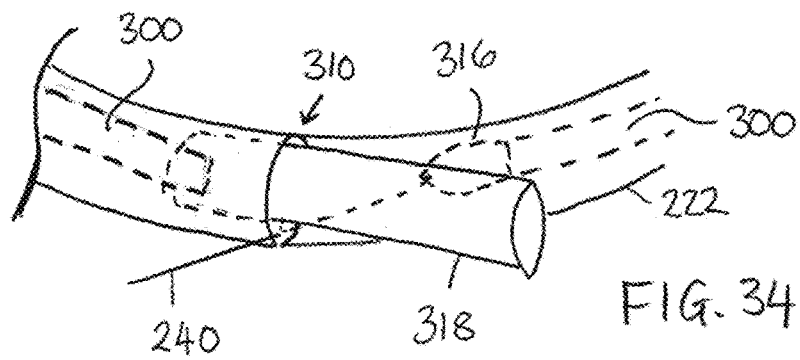
FIG. 34 is a schematic perspective view similar to FIG. 33, but showing near completion of the loading.

Thereafter, the opposite end 240*b* of the loading filament 240 may be pulled manually, to progressively draw the seal component 300 into the accommodation channel 222. Although the component 300 may generally not be enclosed in its own sleeve/cuff, it has been found that in some embodiments the seal component 300 may easily be drawn into the channel 222 by pulling lightly and/or steadily, in a single pulling action. The seal component 300 may be pulled into the channel 222 until the tip advances substantially a full turn around the circumferential length of the channel 222 and abuts the side of the introducer tube 318. The abutting may provide a tactile indication that the sealing component 300 has been loaded into its fully loaded position (FIG. 34).

Figure 35:
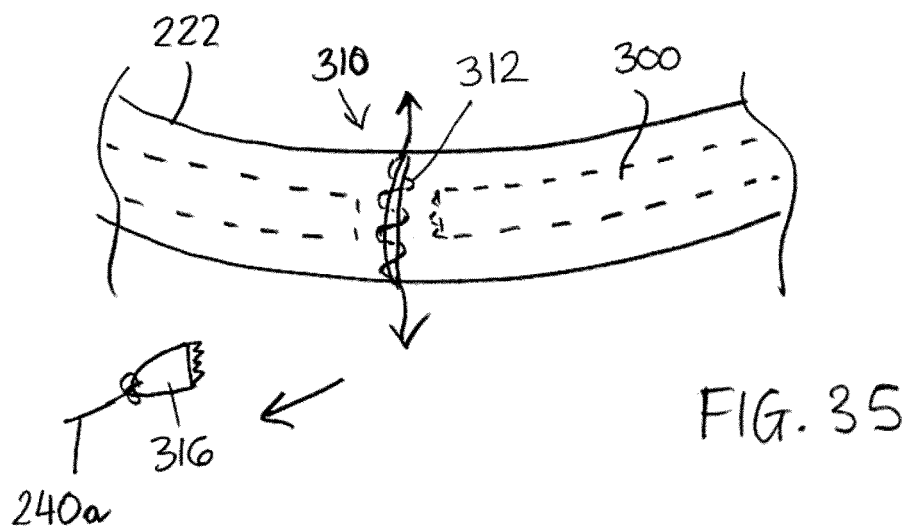
FIG. 35 is a schematic perspective view similar to FIGS. 33 and 34, but showing closing of the accommodation region.

Thereafter, referring to FIG. 35, the introducer tube 318 may be removed, and the tip of the component 300 coupled to the loading filament 240 separated by a brief tearing action. The loading aperture 310 may subsequently be closed by any suitable closure mechanism. In the illustrated example, the purse-string stitch 312 may be pulled tight, to draw the edges of the aperture together in a tightly pursed arrangement effective to seal the channel 222 closed.

Figure 37:
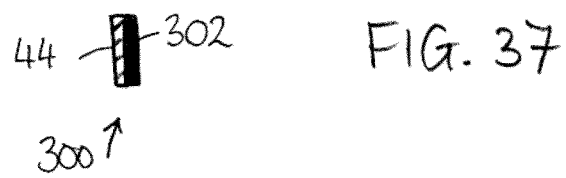
FIG. 37 is a schematic cross-section through a further example of seal component.

Referring to FIG. 37, in some embodiments, the sealing component 300 may optionally include an integral backing 302. The backing 302 may provide structural reinforcement to the sealing member 300. If provided, the backing 302 may optionally be orientated to be on the radially inwardly facing surface of the sealing component 300 once loaded into the channel. The backing may serve to obstruct swelling of the swellable material 44 in a radially inwardly direction (in which might might swell in the apertures of the stent), and instead promote swelling of the swellable material in a radially outward direction into sealing engagement with the surrounding anatomy.

Figure 30:
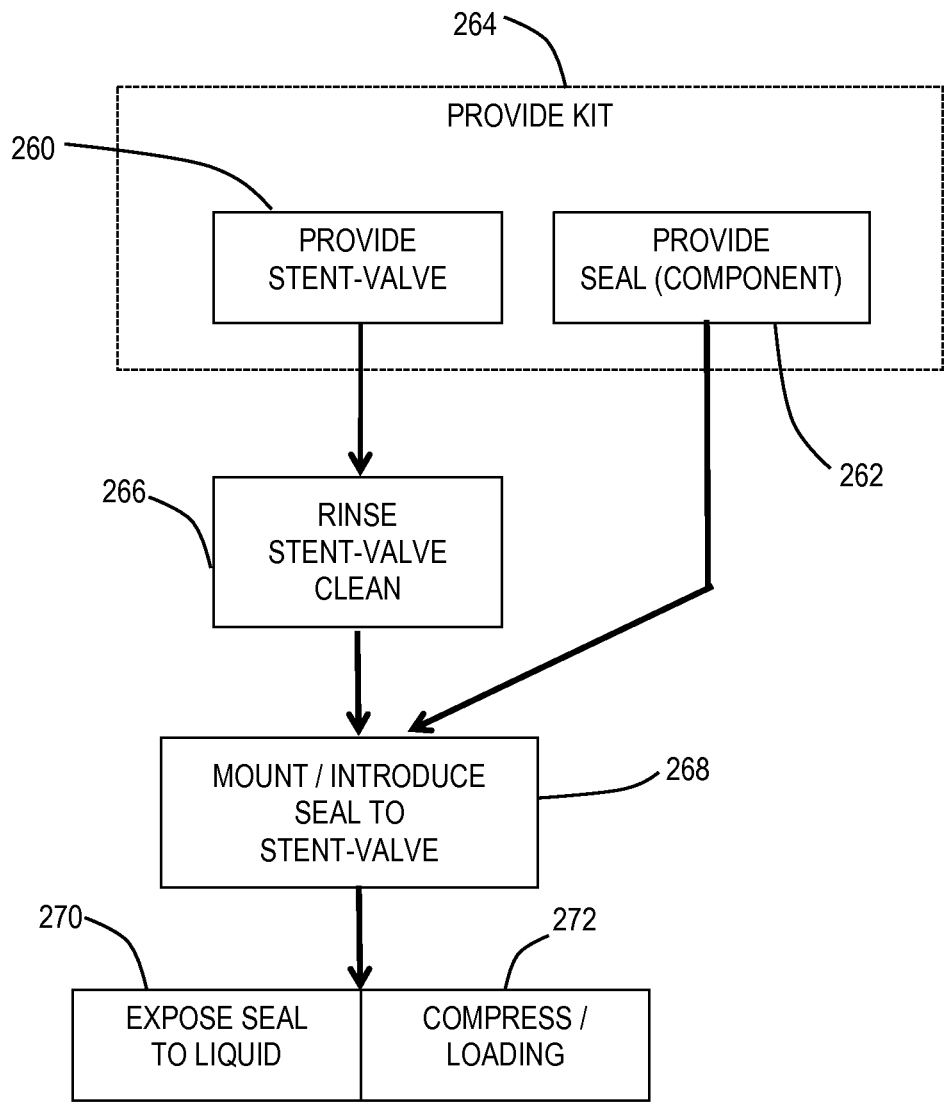
FIG. 30 is a schematic flow diagram showing steps for preparing for use a stent-valve with a separately mountable seal or seal component.

Referring to FIG. 30, an example method of using and/or preparing a stent-valve 10 (especially as described in any of the embodiments of FIGS. 11 to 29) is illustrated.

At step 260 and 262, a stent-valve 10 and at least a component for a seal 40, are provided as separate items. The separate items may optionally be provided as part of a kit (step 264), but nevertheless the at least a component of the seal 40 may be non-integral with the stent-valve 10. Step 260 may comprise providing the stent-valve immersed in a storage and/or sterilization solution, as described above. Step 262 may comprise providing the at least a component for a seal in a dry sterilized state, such as in a sterilized pouch. By providing the at least a component of the seal separately, there is substantially no risk that the seal might be wetted or contaminated by the storage solution in which the stent-valve is stored. A storage compartment or container for the seal may be outside a storage compartment or container for the stent-valve.

At step 266, the stent-valve 10 may be rinsed to remove substantially traces of the storage solution. Step 266 may comprise placing the stent-valve into a bath of a rinsing solution, for example, water or saline. Step 266 may comprise placing the stent-valve into one or more successive baths to provide a multi-stage rinse.

At step 268, the at least a component of the seal may be mounted to, or introduced to or into the stent valve 10. For example, the seal may be loaded into a seal accommodation channel, or the seal may be attached adhesively, or clipped or hooked to the stent-valve. Alternatively, a flowable swelling material may be injected into a seal band.

At step 270, the assembled stent-valve and seal is exposed to liquid while outside the patient's body (e.g. similar to step 94 described previously), and at step 272 the assembled stent-valve is compressed and/or loaded into a delivery catheter (e.g. similar to step 96 described previously). As previously, steps 270 and 272 may be carried out substantially at the same time, or one of the steps may be started before the other in either order, or the steps may be carried out separately in either order.

One loaded into the delivery catheter, the stent-valve 10 may be implanted using a method, for example, similar or the same as that of FIG. 10.

Although the foregoing description has described the embodiments in terms of a stent-valve 10, it will be appreciated that many of the same techniques may be applied to other (e.g. stented) prostheses.

It is emphasized that the foregoing description of preferred embodiments does not limit the scope of the invention, and that many alternatives, modifications, and improvements may be made within the scope and/or principles of the invention.

The invention claimed is:

1. An apparatus configured for delivery from a delivery catheter, comprising:
    a stent-valve disposable, in a compressed configuration, within the delivery catheter, the stent-valve comprising an accommodation region for accommodating a seal component to form a seal around the exterior of the stent-valve, and the stent-valve being expandable from the compressed configuration to an operative configuration after delivery from the delivery catheter;
    the seal component comprising swellable material that swells in response to contact with blood or a blood component, the seal component being mountable and/or introducible to the accommodation region to form a combined assembly with the stent-valve, in the compressed configuration, prior to delivery of the stent-valve from the delivery catheter;
    wherein the accommodation region comprises an accommodation channel configured to receive the seal component therein, the accommodation channel being attached to the exterior of the stent-valve; and
    a loading filament slidably disposed within the accommodation channel along a predefined path extending circumferentially around the stent-valve, the loading filament being configured to circumferentially pull the seal component into the accommodation channel along the predefined path thereby forming the combined assembly;
    wherein the combined assembly is disposed within the delivery catheter prior to delivery.

2. The apparatus of claim 1, wherein the accommodation channel is a continuous accommodation channel.

3. The apparatus of claim 1, wherein the seal component comprises a tube surrounding the swellable material.

4. The apparatus of claim 1, wherein the seal component comprises exposed swellable material.

5. The apparatus of claim 1, wherein the accommodation channel defines a cuff for confining the swellable material in use.

6. The apparatus of claim 1, further comprising an introducer tube for facilitating mounting or introduction of the seal component to the stent-valve.

7. The apparatus of claim 1, wherein the accommodation channel is a discontinuous accommodation channel.

8. The apparatus of claim 7, wherein the accommodation channel is formed by a series of spaced-apart loops disposed circumferentially about the stent-valve.

9. The apparatus of claim 1, wherein the stent-valve includes a stent having an inflow portion and an outflow portion each formed by a lattice structure of the stent, and a plurality of stabilization arches extending downstream from the outflow portion.

10. The apparatus of claim 9, wherein the inflow portion includes an extremity formed with a zig-zag shape comprising upstream apexes and downstream apexes;

wherein the accommodation region is disposed between the downstream apexes and the outflow portion.

\* \* \* \* \*